(12) United States Patent    (10) Patent No.: US 7,819,912 B2
Shanley                      (45) Date of Patent: *Oct. 26, 2010

(54) EXPANDABLE MEDICAL DEVICE WITH BENEFICIAL AGENT DELIVERY MECHANISM

(75) Inventor: John F. Shanley, Redwood City, CA (US)

(73) Assignee: Innovational Holdings LLC, New Brunswick, NJ (US)

( * ) Notice: Subject to any disclaimer, the term of this patent is extended or adjusted under 35 U.S.C. 154(b) by 1675 days.

This patent is subject to a terminal disclaimer.

(21) Appl. No.: 10/379,983

(22) Filed: Mar. 4, 2003

(65) Prior Publication Data

US 2003/0167085 A1    Sep. 4, 2003

Related U.S. Application Data

(63) Continuation of application No. 09/649,217, filed on Aug. 28, 2000, now Pat. No. 6,562,065, which is a continuation of application No. 09/183,555, filed on Oct. 29, 1998, now Pat. No. 6,241,762.

(60) Provisional application No. 60/079,881, filed on Mar. 30, 1998.

(51) Int. Cl.
*A61F 2/06* (2006.01)
*A61M 29/00* (2006.01)

(52) U.S. Cl. ...................... 623/1.15; 606/198

(58) Field of Classification Search ............... 623/1.15, 623/1.16, 1.2; 606/108, 198
See application file for complete search history.

(56) References Cited

U.S. PATENT DOCUMENTS 3,657,744 A    4/1972 Ersek
4,300,244 A   11/1981 Bukros
4,531,936 A    7/1985 Gordon (Continued)

FOREIGN PATENT DOCUMENTS

CA    2234787 A1    4/1998

(Continued)

OTHER PUBLICATIONS

Marx, Steven O. et al., Rapamycin-FKBP Inhibits Cell Cycle Regulators of Proliferation in Vascular Smooth Muscle Cells, Circulation Research, 1995;76(3):412-417.

(Continued)

*Primary Examiner*—Vy Q Bui

(57) ABSTRACT

An expandable tissue supporting device of the present invention employs ductile hinges at selected points in the expandable device. When expansion forces are applied to the device as a whole, the ductile hinges concentrate expansion stresses and strains in small well defined areas. The expandable medical device including ductile hinges provides the advantages of low expansion force requirements, relatively thick walls which are radio-opaque, improved crimping properties, high crush strength, reduced elastic recoil after implantation, and control of strain to a desired level. The expandable tissue supporting device includes a plurality of elongated beams arranged in a cylindrical device and connected together by a plurality of ductile hinges. Although many ductile hinge configurations are possible, the ductile hinges preferably have a substantially constant hinge cross sectional area which is smaller than a beam cross sectional area such that as the device is expanded from a first diameter to a second diameter, the ductile hinges experience plastic deformation while the beams are not plastically deformed.

16 Claims, 10 Drawing Sheets

U.S. PATENT DOCUMENTS

| | | | |
|---|---|---|---|
| 4,542,025 A | 9/1985 | Tice et al. | |
| 4,580,568 A | 4/1986 | Gianturco | |
| 4,650,466 A | 3/1987 | Luther | |
| 4,733,665 A | 3/1988 | Palmaz | |
| 4,739,762 A | 4/1988 | Palmaz | |
| 4,776,337 A | 10/1988 | Palmaz | |
| 4,800,882 A | 1/1989 | Gianturco | |
| 4,824,436 A | 4/1989 | Wollinsky | |
| 4,834,755 A | 5/1989 | Silvestrini et al. | |
| 4,889,119 A | 12/1989 | Jamiolkowski et al. | |
| 4,916,193 A | 4/1990 | Tang et al. | |
| 4,955,878 A | 9/1990 | See et al. | |
| 4,957,508 A | 9/1990 | Kaneko et al. | |
| 4,960,790 A | 10/1990 | Steela et al. | |
| 4,969,458 A | 11/1990 | Witkor | |
| 4,989,601 A | 2/1991 | Marchosky et al. | |
| 4,990,155 A | 2/1991 | Wilkoff | |
| 4,994,071 A | 2/1991 | MacGregor | |
| 5,017,381 A | 5/1991 | Maruyama et al. | |
| 5,019,090 A | 5/1991 | Pinchuk | |
| 5,049,132 A | 9/1991 | Shaffer et al. | |
| 5,053,048 A | 10/1991 | Pinchuk | |
| 5,059,166 A | 10/1991 | Fischell et al. | |
| 5,059,178 A | 10/1991 | Ya et al. | |
| 5,059,211 A | 10/1991 | Stack et al. | |
| 5,078,726 A | 1/1992 | Kreamer | |
| 5,085,629 A | 2/1992 | Goldberg et al. | |
| 5,092,841 A | 3/1992 | Spears | |
| 5,102,417 A | 4/1992 | Palmaz | |
| 5,139,480 A | 8/1992 | Hickle et al. | |
| 5,157,049 A | 10/1992 | Haugwitz et al. | |
| 5,160,341 A | 11/1992 | Brenneman et al. | |
| 5,171,217 A | 12/1992 | March et al. | |
| 5,171,262 A | 12/1992 | MacGregor | |
| 5,176,617 A | 1/1993 | Fischell et al. | |
| 5,195,984 A | 3/1993 | Schatz | |
| 5,197,978 A | 3/1993 | Hess | |
| 5,213,580 A | 5/1993 | Slepian et al. | |
| 5,223,092 A | 6/1993 | Grinnell et al. | |
| 5,234,456 A | 8/1993 | Silvestrini | |
| 5,242,399 A | 9/1993 | Lau et al. | |
| 5,282,823 A | 2/1994 | Schwartz et al. | |
| 5,283,257 A | 2/1994 | Gregory et al. | |
| 5,286,254 A | 2/1994 | Shapland et al. | |
| 5,288,711 A | 2/1994 | Mitchell et al. | |
| 5,290,271 A | 3/1994 | Jernberg | |
| 5,292,512 A | 3/1994 | Schaefer et al. | |
| 5,304,121 A | 4/1994 | Sahatjian | |
| 5,314,688 A | 5/1994 | Kauffman et al. | |
| 5,342,348 A | 8/1994 | Kaplan | |
| 5,342,621 A | 8/1994 | Eury | |
| 5,344,426 A | 9/1994 | Lau et al. | |
| 5,380,299 A | 1/1995 | Fearnot et al. | |
| 5,383,892 A | 1/1995 | Cardon et al. | |
| 5,383,928 A | 1/1995 | Scott et al. | |
| 5,403,858 A | 4/1995 | Bastard et al. | |
| 5,407,683 A | 4/1995 | Shively | |
| 5,415,869 A | 5/1995 | Straubinger et al. | |
| 5,419,760 A | 5/1995 | Narciso | |
| 5,439,446 A | 8/1995 | Barry | |
| 5,439,466 A | 8/1995 | Barry | |
| 5,439,686 A | 8/1995 | Desai et al. | |
| 5,441,515 A | 8/1995 | Khosravi et al. | |
| 5,441,745 A | 8/1995 | Presant et al. | |
| 5,443,458 A | 8/1995 | Eury | |
| 5,443,496 A | 8/1995 | Schwartz et al. | |
| 5,443,497 A | 8/1995 | Venbrx | |
| 5,443,500 A | 8/1995 | Sigwart | |
| 5,447,724 A | 9/1995 | Helmus et al. | |
| 5,449,373 A | 9/1995 | Pinchasik et al. | |
| 5,449,382 A | 9/1995 | Dayton | |
| 5,449,513 A | 9/1995 | Yokoyama et al. | |
| 5,457,113 A | 10/1995 | Cullinan et al. | |
| 5,460,817 A | 10/1995 | Langley et al. | |
| 5,462,866 A | 10/1995 | Wang | |
| 5,464,450 A | 11/1995 | Buscemi et al. | |
| 5,464,650 A | 11/1995 | Berg et al. | |
| 5,472,985 A | 12/1995 | Grainger et al. | |
| 5,473,055 A | 12/1995 | Mongelli et al. | |
| 5,496,365 A | 3/1996 | Sgro | |
| 5,499,373 A | 3/1996 | Richards et al. | |
| 5,500,013 A | 3/1996 | Buscemi et al. | |
| 5,510,077 A | 4/1996 | Dinh et al. | |
| 5,512,055 A | 4/1996 | Domb et al. | |
| 5,516,781 A | 5/1996 | Morris et al. | |
| 5,519,954 A | 5/1996 | Garrett | |
| 5,523,092 A | 6/1996 | Hanson et al. | |
| 5,527,344 A | 6/1996 | Arzbaecher et al. | |
| 5,534,287 A | 7/1996 | Lukic | |
| 5,545,208 A | 8/1996 | Wolff et al. | |
| 5,545,210 A | 8/1996 | Hess et al. | |
| 5,545,569 A | 8/1996 | Grainger et al. | |
| 5,551,954 A | 9/1996 | Buscemi et al. | |
| 5,554,182 A | 9/1996 | Dinh et al. | |
| 5,556,413 A | 9/1996 | Lam | |
| 5,562,922 A | 10/1996 | Lambert | |
| 5,563,146 A | 10/1996 | Morris et al. | |
| 5,571,089 A | 11/1996 | Crocker | |
| 5,571,166 A | 11/1996 | Dinh et al. | |
| 5,575,571 A | 11/1996 | Takebayashi et al. | |
| 5,578,075 A | 11/1996 | Dayton | |
| 5,591,197 A | 1/1997 | Orth et al. | |
| 5,591,224 A | 1/1997 | Schwartz et al. | |
| 5,591,227 A | 1/1997 | Dinh et al. | |
| 5,593,434 A | 1/1997 | Williams | |
| 5,595,722 A | 1/1997 | Grainger et al. | |
| 5,599,352 A | 2/1997 | Dinh et al. | |
| 5,599,722 A | 2/1997 | Grainger et al. | |
| 5,599,844 A | 2/1997 | Grainger et al. | |
| 5,603,722 A | 2/1997 | Phan et al. | |
| 5,605,696 A | 2/1997 | Eury et al. | |
| 5,607,442 A | 3/1997 | Fischell et al. | |
| 5,607,463 A | 3/1997 | Schwartz et al. | |
| 5,607,475 A | 3/1997 | Cahalan et al. | |
| 5,609,626 A | 3/1997 | Quijano et al. | |
| 5,609,629 A | 3/1997 | Fearnot et al. | |
| 5,616,608 A | 4/1997 | Kinsella et al. | |
| 5,617,878 A | 4/1997 | Taheri | |
| 5,618,299 A | 4/1997 | Khosravi et al. | |
| 5,624,411 A | 4/1997 | Tuch | |
| 5,628,785 A | 5/1997 | Schwartz et al. | |
| 5,628,787 A | 5/1997 | Mayer | |
| 5,629,077 A | 5/1997 | Turnlund et al. | |
| 5,632,840 A | 5/1997 | Campbell | |
| 5,637,113 A | 6/1997 | Tartaglia et al. | |
| 5,643,314 A | 7/1997 | Carpenter et al. | |
| 5,646,160 A | 7/1997 | Morris et al. | |
| 5,649,977 A | 7/1997 | Campbell | |
| 5,651,174 A | 7/1997 | Schwartz et al. | |
| 5,660,873 A | 8/1997 | Nikolaychik et al. | |
| 5,665,591 A | 9/1997 | Sonenshein et al. | |
| 5,667,764 A | 9/1997 | Kopia et al. | |
| 5,670,161 A | 9/1997 | Healy et al. | |
| 5,670,659 A | 9/1997 | Alas et al. | |
| 5,672,638 A | 9/1997 | Verhoeven et al. | |
| 5,674,241 A | 10/1997 | Bley et al. | |
| 5,674,242 A | 10/1997 | Phan et al. | |
| 5,674,278 A | 10/1997 | Boneau | |
| 5,679,400 A | 10/1997 | Tuch | |
| 5,679,659 A | 10/1997 | Verhoeven et al. | |
| 5,693,085 A | 12/1997 | Buirge et al. | |
| 5,697,967 A | 12/1997 | Dinh et al. | |
| 5,697,971 A | 12/1997 | Fischell et al. | |
| 5,700,286 A | 12/1997 | Tartaglia et al. | |

| | | | | | |
|---|---|---|---|---|---|
| 5,707,385 A | 1/1998 | Williams | 5,980,972 A | 11/1999 | Ding |
| 5,713,949 A | 2/1998 | Jayaranman | 5,981,568 A | 11/1999 | Kunz et al. |
| 5,716,981 A | 2/1998 | Hunter et al. | 5,984,957 A | 11/1999 | Laptewicz, Jr. et al. |
| 5,722,979 A | 3/1998 | Kusleika | 5,992,769 A | 11/1999 | Wise et al. |
| 5,725,548 A | 3/1998 | Jayaraman | 5,994,341 A | 11/1999 | Hunter et al. |
| 5,725,549 A | 3/1998 | Lam | 6,007,517 A | 12/1999 | Anderson |
| 5,725,567 A | 3/1998 | Wolff et al. | 6,015,432 A | 1/2000 | Rakos et al. |
| 5,728,150 A | 3/1998 | McDonald et al. | 6,017,362 A | 1/2000 | Lau |
| 5,728,420 A | 3/1998 | Keogh | 6,017,363 A | 1/2000 | Hojeibane |
| 5,733,327 A | 3/1998 | Igaki et al. | 6,019,789 A | 2/2000 | Dinh et al. |
| 5,733,330 A | 3/1998 | Cox | 6,022,371 A | 2/2000 | Killion |
| 5,733,925 A | 3/1998 | Kunz et al. | 6,024,740 A | 2/2000 | Lesh et al. |
| 5,735,897 A | 4/1998 | Buirge | 6,027,526 A | 2/2000 | Limon et al. |
| 5,741,293 A | 4/1998 | Wijay | 6,030,414 A | 2/2000 | Taheri |
| 5,744,460 A | 4/1998 | Muller et al. | 6,042,606 A | 3/2000 | Frantzen |
| 5,755,772 A | 5/1998 | Evans et al. | 6,056,722 A | 5/2000 | Jayaraman |
| 5,766,239 A | 6/1998 | Cox | 6,063,101 A | 5/2000 | Jacobsen et al. |
| 5,769,883 A | 6/1998 | Buscemi et al. | 6,071,305 A | 6/2000 | Brown et al. |
| 5,770,609 A | 6/1998 | Grainger et al. | 6,074,659 A | 6/2000 | Kunz et al. |
| 5,773,479 A | 6/1998 | Grainger et al. | 6,083,258 A | 7/2000 | Yadav |
| 5,776,162 A | 7/1998 | Kleshinski | 6,086,582 A | 7/2000 | Altman et al. |
| 5,776,181 A | 7/1998 | Lee et al. | 6,087,479 A | 7/2000 | Stamler et al. |
| 5,776,184 A | 7/1998 | Tuch | 6,099,561 A | 8/2000 | Alt |
| 5,782,908 A | 7/1998 | Cahalan et al. | 6,099,562 A | 8/2000 | Ding et al. |
| 5,788,979 A | 8/1998 | Alt et al. | 6,117,101 A | 9/2000 | Diederich et al. |
| 5,792,106 A | 8/1998 | Mische | 6,120,535 A | 9/2000 | McDonald et al. |
| 5,797,898 A | 8/1998 | Santini, Jr. et al. | 6,120,536 A | 9/2000 | Ding et al. |
| 5,799,384 A | 9/1998 | Schwartz et al. | 6,120,847 A | 9/2000 | Yang et al. |
| 5,800,507 A | 9/1998 | Schwartz | 6,121,027 A | 9/2000 | Clapper et al. |
| 5,811,447 A | 9/1998 | Kunz et al. | 6,123,861 A | 9/2000 | Santini, Jr. et al. |
| 5,817,152 A | 10/1998 | Birdsall et al. | 6,140,127 A | 10/2000 | Sprague |
| 5,820,917 A | 10/1998 | Tuch | 6,153,252 A | 11/2000 | Hossainy et al. |
| 5,820,918 A | 10/1998 | Ronan et al. | 6,156,062 A | 12/2000 | McGuinness |
| 5,824,045 A | 10/1998 | Alt | 6,159,488 A | 12/2000 | Nagler et al. |
| 5,824,048 A | 10/1998 | Tuch | 6,171,609 B1 | 1/2001 | Kunz |
| 5,824,049 A | 10/1998 | Ragheb et al. | 6,174,325 B1 | 1/2001 | Kitaoka et al. |
| 5,827,322 A | 10/1998 | Williams | 6,193,746 B1 | 2/2001 | Strecker |
| 5,833,651 A | 11/1998 | Donovan et al. | 6,206,914 B1 | 3/2001 | Soykan et al. |
| 5,837,008 A | 11/1998 | Berg et al. | 6,206,916 B1 | 3/2001 | Furst |
| 5,837,313 A | 11/1998 | Ding et al. | 6,231,600 B1 | 5/2001 | Zhong |
| 5,843,117 A | 12/1998 | Alt et al. | 6,239,118 B1 | 5/2001 | Schatz et al. |
| 5,843,120 A | 12/1998 | Israel et al. | 6,240,616 B1 | 6/2001 | Yan |
| 5,843,166 A | 12/1998 | Lentz et al. | 6,241,762 B1 | 6/2001 | Shanley |
| 5,843,172 A | 12/1998 | Yan | 6,245,101 B1 | 6/2001 | Drasler et al. |
| 5,843,175 A | 12/1998 | Frantzen | 6,249,952 B1 | 6/2001 | Ding |
| 5,843,741 A | 12/1998 | Wong et al. | 6,254,632 B1 * | 7/2001 | Wu et al. ................ 623/1.15 |
| 5,849,034 A | 12/1998 | Schwartz | 6,261,318 B1 | 7/2001 | Lee et al. |
| 5,851,217 A | 12/1998 | Wolff et al. | 6,268,390 B1 | 7/2001 | Kunz |
| 5,851,231 A | 12/1998 | Wolff et al. | 6,273,908 B1 * | 8/2001 | Ndondo-Lay ............ 623/1.43 |
| 5,853,419 A | 12/1998 | Imran | 6,273,910 B1 | 8/2001 | Limon |
| 5,855,600 A | 1/1999 | Alt | 6,273,911 B1 | 8/2001 | Cox et al. |
| 5,865,814 A | 2/1999 | Tuch | 6,273,913 B1 | 8/2001 | Wright et al. |
| 5,868,781 A | 2/1999 | Killion | 6,280,411 B1 | 8/2001 | Lennox |
| 5,871,535 A | 2/1999 | Wolff et al. | 6,287,332 B1 | 9/2001 | Bolz et al. |
| 5,876,419 A | 3/1999 | Carpenter et al. | 6,290,673 B1 | 9/2001 | Shanley |
| 5,879,697 A | 3/1999 | Ding et al. | 6,293,967 B1 | 9/2001 | Shanley |
| 5,882,335 A | 3/1999 | Leone et al. | 6,299,604 B1 | 10/2001 | Ragheb et al. |
| 5,886,026 A | 3/1999 | Hunter et al. | 6,306,166 B1 | 10/2001 | Barry et al. |
| 5,891,108 A | 4/1999 | Leone et al. | 6,306,421 B1 | 10/2001 | Kunz et al. |
| 5,893,840 A | 4/1999 | Hull et al. | 6,309,414 B1 | 10/2001 | Rolando et al. |
| 5,922,020 A | 7/1999 | Klein et al. | 6,312,459 B1 | 11/2001 | Huang et al. |
| 5,922,021 A | 7/1999 | Jang | 6,312,460 B2 | 11/2001 | Drasler et al. |
| 5,928,916 A | 7/1999 | Keogh | 6,338,739 B1 | 1/2002 | Datta et al. |
| 5,932,243 A | 8/1999 | Fricker et al. | 6,358,556 B1 | 3/2002 | Ding et al. |
| 5,935,506 A | 8/1999 | Schmitz et al. | 6,358,989 B1 | 3/2002 | Kunz et al. |
| 5,945,456 A | 8/1999 | Grainger et al. | 6,368,346 B1 | 4/2002 | Jadhav |
| 5,957,971 A | 9/1999 | Schwartz | 6,369,039 B1 | 4/2002 | Palasis et al. |
| 5,964,798 A | 10/1999 | Imran | 6,379,381 B1 | 4/2002 | Hossainy et al. |
| 5,968,091 A | 10/1999 | Pinchuk et al. | 6,387,124 B1 | 5/2002 | Buscemi et al. |
| 5,968,092 A | 10/1999 | Buscemi et al. | 6,395,326 B1 | 5/2002 | Castro et al. |
| 5,972,027 A | 10/1999 | Johnson | 6,399,144 B2 | 6/2002 | Dinh et al. |
| 5,976,182 A | 11/1999 | Cox | 6,403,635 B1 | 6/2002 | Kinsella et al. |
| 5,980,551 A | 11/1999 | Summers et al. | 6,423,092 B2 | 7/2002 | Datta et al. |

| Patent Number | Date | Inventor(s) |
|---|---|---|
| 6,423,345 B2 | 7/2002 | Bernstein et al. |
| 6,429,232 B1 | 8/2002 | Kinsella et al. |
| 6,451,051 B2 | 9/2002 | Drasler et al. |
| 6,461,631 B1 | 10/2002 | Dunn et al. |
| 6,468,302 B2 | 10/2002 | Cox et al. |
| 6,475,237 B2 | 11/2002 | Drasler et al. |
| 6,482,810 B1 | 11/2002 | Brem et al. |
| 6,491,617 B1 | 12/2002 | Ogle et al. |
| 6,491,666 B1 | 12/2002 | Santini, Jr. et al. |
| 6,491,938 B2 | 12/2002 | Kunz et al. |
| 6,497,916 B1 | 12/2002 | Taylor et al. |
| 6,500,859 B2 | 12/2002 | Kinsella et al. |
| 6,503,954 B1 | 1/2003 | Bhat et al. |
| 6,506,411 B2 | 1/2003 | Hunter et al. |
| 6,506,437 B1 | 1/2003 | Harish et al. |
| 6,511,505 B2 | 1/2003 | Cox et al. |
| 6,515,009 B1 | 2/2003 | Kunz et al. |
| 6,528,121 B2 | 3/2003 | Ona et al. |
| 6,530,950 B1 | 3/2003 | Alvarado et al. |
| 6,530,951 B1 | 3/2003 | Bates et al. |
| 6,533,807 B2 | 3/2003 | Wolinsky et al. |
| 6,537,256 B2 | 3/2003 | Santini et al. |
| 6,540,774 B1 | 4/2003 | Cox |
| 6,544,544 B2 | 4/2003 | Hunter et al. |
| 6,551,303 B1 | 4/2003 | Van Tassel et al. |
| 6,551,838 B2 | 4/2003 | Santini, Jr. et al. |
| 6,558,733 B1 | 5/2003 | Hossainy et al. |
| 6,562,065 B1 | 5/2003 | Shanley |
| 6,565,602 B2 | 5/2003 | Rolando et al. |
| 6,569,441 B2 | 5/2003 | Kunz et al. |
| 6,569,688 B2 | 5/2003 | Sivan et al. |
| 6,572,642 B2 | 6/2003 | Rinaldi et al. |
| 6,585,764 B2 | 7/2003 | Wright et al. |
| 6,585,765 B1 | 7/2003 | Hossainy et al. |
| 6,585,773 B1 | 7/2003 | Xie |
| 6,599,314 B2 | 7/2003 | Mathis |
| 6,599,928 B2 | 7/2003 | Kunz et al. |
| 6,602,284 B2 | 8/2003 | Cox et al. |
| 6,613,084 B2 | 9/2003 | Yang |
| 6,616,690 B2 | 9/2003 | Rolando et al. |
| 6,627,246 B2 | 9/2003 | Mehta et al. |
| 6,638,302 B1 | 10/2003 | Curcio et al. |
| 6,645,547 B1 | 11/2003 | Shekalim et al. |
| 6,656,162 B2 | 12/2003 | Santini, Jr. et al. |
| 6,656,217 B1 | 12/2003 | Herzog, Jr. et al. |
| 6,663,664 B1 | 12/2003 | Pacetti |
| 6,663,881 B2 | 12/2003 | Kunz et al. |
| 6,673,385 B1 | 1/2004 | Ding et al. |
| 6,682,545 B1 | 1/2004 | Kester |
| 6,689,390 B2 | 2/2004 | Bernstein et al. |
| 6,702,850 B1 | 3/2004 | Byun et al. |
| 6,706,061 B1 | 3/2004 | Fischell et al. |
| 6,712,845 B2 | 3/2004 | Hossainy |
| 6,713,119 B2 | 3/2004 | Hossainy et al. |
| 6,716,242 B1 | 4/2004 | Altman |
| 6,716,444 B1 | 4/2004 | Castro et al. |
| 6,716,981 B2 | 4/2004 | Hunter et al. |
| 6,720,350 B2 | 4/2004 | Kunz et al. |
| 6,723,373 B1 | 4/2004 | Narayanan et al. |
| 6,730,064 B2 | 5/2004 | Ragheb et al. |
| 6,730,116 B1 | 5/2004 | Wolinsky et al. |
| 6,746,773 B2 | 6/2004 | Llanos et al. |
| 6,753,071 B1 | 6/2004 | Pacetti |
| 6,764,507 B2 | 7/2004 | Shanley |
| 6,780,424 B2 | 8/2004 | Claude |
| 6,783,793 B1 | 8/2004 | Hossainy et al. |
| 6,790,228 B2 | 9/2004 | Hossainy et al. |
| 6,818,063 B1 | 11/2004 | Kerrigan |
| 6,846,841 B2 | 1/2005 | Hunter et al. |
| 6,855,770 B2 | 2/2005 | Pinchuk et al. |
| 6,860,946 B2 | 3/2005 | Hossainy et al. |
| 6,861,088 B2 | 3/2005 | Weber et al. |
| 6,869,443 B2 | 3/2005 | Buscemi et al. |
| 6,887,510 B2 | 5/2005 | Villareal |
| 6,890,339 B2 | 5/2005 | Sahatjian et al. |
| 6,896,965 B1 | 5/2005 | Hossainy |
| 6,908,622 B2 | 6/2005 | Barry et al. |
| 6,908,624 B2 | 6/2005 | Hossainy et al. |
| 6,939,376 B2 | 9/2005 | Shulze et al. |
| 6,964,680 B2 | 11/2005 | Shanley |
| 7,192,438 B2 | 3/2007 | Margolis |
| 7,195,628 B2 | 3/2007 | Falkenberg |
| 7,429,268 B2 | 9/2008 | Shanley et al. |
| 2001/0000802 A1 | 5/2001 | Soykan et al. |
| 2001/0018469 A1 | 8/2001 | Chen et al. |
| 2001/0027340 A1 | 10/2001 | Wright et al. |
| 2001/0029351 A1 | 10/2001 | Falotico et al. |
| 2001/0034363 A1 | 10/2001 | Li et al. |
| 2001/0044648 A1 | 11/2001 | Wolinsky et al. |
| 2001/0044652 A1 | 11/2001 | Moore |
| 2002/0002400 A1 | 1/2002 | Drasler et al. |
| 2002/0005206 A1 | 1/2002 | Falotico et al. |
| 2002/0007209 A1 | 1/2002 | Scheerder et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0016625 A1 | 2/2002 | Falotico et al. |
| 2002/0022876 A1 | 2/2002 | Richter et al. |
| 2002/0028243 A1 | 3/2002 | Masters |
| 2002/0032414 A1 | 3/2002 | Ragheb et al. |
| 2002/0038145 A1 | 3/2002 | Jang |
| 2002/0041931 A1 | 4/2002 | Suntola et al. |
| 2002/0068969 A1 | 6/2002 | Shanley et al. |
| 2002/0071902 A1 | 6/2002 | Ding et al. |
| 2002/0072511 A1 | 6/2002 | New et al. |
| 2002/0082679 A1 | 6/2002 | Sirhan et al. |
| 2002/0082680 A1 | 6/2002 | Shanley et al. |
| 2002/0082682 A1 | 6/2002 | Barclay et al. |
| 2002/0094985 A1 | 7/2002 | Hermann et al. |
| 2002/0123801 A1 | 9/2002 | Pacetti et al. |
| 2002/0127263 A1 | 9/2002 | Carlyle et al. |
| 2002/0128704 A1 | 9/2002 | Daum et al. |
| 2002/0142039 A1 | 10/2002 | Claude |
| 2002/0155212 A1 | 10/2002 | Hossainy |
| 2002/0193475 A1 | 12/2002 | Hossainy et al. |
| 2003/0004141 A1 | 1/2003 | Brown |
| 2003/0004564 A1 | 1/2003 | Elkins et al. |
| 2003/0018083 A1 | 1/2003 | Jerussi et al. |
| 2003/0028244 A1 | 2/2003 | Bates et al. |
| 2003/0036794 A1 | 2/2003 | Ragheb et al. |
| 2003/0050687 A1 | 3/2003 | Schwade et al. |
| 2003/0060877 A1 | 3/2003 | Falotico et al. |
| 2003/0068355 A1 | 4/2003 | Shanley et al. |
| 2003/0069606 A1 | 4/2003 | Girouard et al. |
| 2003/0077312 A1 | 4/2003 | Schmulewicz et al. |
| 2003/0083646 A1 | 5/2003 | Sirhan et al. |
| 2003/0086957 A1 | 5/2003 | Hughes et al. |
| 2003/0088307 A1 | 5/2003 | Shulze et al. |
| 2003/0100865 A1 | 5/2003 | Santini et al. |
| 2003/0125803 A1 | 7/2003 | Vallana et al. |
| 2003/0157241 A1 | 8/2003 | Hossainy et al. |
| 2003/0176915 A1 | 9/2003 | Wright et al. |
| 2003/0181973 A1 | 9/2003 | Sahota |
| 2003/0199970 A1 | 10/2003 | Shanley |
| 2003/0216699 A1 | 11/2003 | Falotico |
| 2004/0073296 A1 | 4/2004 | Epstein et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2005/0059991 A1 | 3/2005 | Shanley |
| 2005/0119720 A1 | 6/2005 | Gale et al. |
| 2005/0137678 A1 | 6/2005 | Varma |
| 2007/0067026 A1 | 3/2007 | Shanley |
| 2008/0097579 A1 | 4/2008 | Shanley et al. |
| 2008/0097583 A1 | 4/2008 | Shanley et al. |

| | | | |
|---|---|---|---|
| 2008/0109071 A1 | 5/2008 | Shanley | |
| 2008/0243070 A1 | 10/2008 | Shanley | |
| 2008/0249609 A1 | 10/2008 | Shanley | |

FOREIGN PATENT DOCUMENTS

| | | | |
|---|---|---|---|
| CA | 2323358 A | 10/1999 | |
| CA | 2409787 A | 12/2001 | |
| EP | 0 294 905 B1 | 12/1988 | |
| EP | 0 335 341 B1 | 10/1989 | |
| EP | 0 374 698 A2 | 6/1990 | |
| EP | 0 470 246 B1 | 2/1992 | |
| EP | 0 470 569 B1 | 2/1992 | |
| EP | 0 543 653 A1 | 5/1993 | |
| EP | 0 551 182 B1 | 7/1993 | |
| EP | 0 556 245 B1 | 8/1993 | |
| EP | 0566807 | 10/1993 | |
| EP | 0 567 816 A1 | 11/1993 | |
| EP | 0 568 310 A | 11/1993 | |
| EP | 0 604 022 A1 | 6/1994 | |
| EP | 0 623 354 B1 | 11/1994 | |
| EP | 0 627 226 B1 | 12/1994 | |
| EP | 0 679 373 B1 | 11/1995 | |
| EP | 0 706 376 B1 | 4/1996 | |
| EP | 0 712 615 | 5/1996 | |
| EP | 0 716 836 | 6/1996 | |
| EP | 0 716 836 B1 | 6/1996 | |
| EP | 0 734 698 B1 | 10/1996 | |
| EP | 0 747 069 | 12/1996 | |
| EP | 0 752 885 B1 | 1/1997 | |
| EP | 0 761 251 | 3/1997 | |
| EP | 0 761 251 A | 3/1997 | |
| EP | 0 706 376 B1 | 4/1997 | |
| EP | 0 770 401 B1 | 5/1997 | |
| EP | 0 797 963 A2 | 10/1997 | |
| EP | 0 809 515 B1 | 12/1997 | |
| EP | 0 832 655 B1 | 4/1998 | |
| EP | 0 850 651 | 7/1998 | |
| EP | 0 850 651 B1 | 7/1998 | |
| EP | 0 897 700 B1 | 2/1999 | |
| EP | 0 934 036 B1 | 8/1999 | |
| EP | 0 938 878 A | 9/1999 | |
| EP | 0 938 878 B1 | 9/1999 | |
| EP | 0 566 245 B1 | 10/1999 | |
| EP | 0 950 386 A | 10/1999 | |
| EP | 0 959 812 B1 | 12/1999 | |
| EP | 0 980 280 B1 | 2/2000 | |
| EP | 1 118 325 | 7/2001 | |
| EP | 1 118 325 B1 | 7/2001 | |
| EP | 1132058 A1 | 9/2001 | |
| EP | 1 172 074 A2 | 1/2002 | |
| EP | 1 181 943 A1 | 2/2002 | |
| EP | 1 189 554 B1 | 3/2002 | |
| EP | 1 223 305 B1 | 7/2002 | |
| EP | 1222941 | 7/2002 | |
| EP | 1 236 478 B1 | 9/2002 | |
| EP | 0 711 158 B1 | 3/2003 | |
| EP | 0 375 520 B1 | 4/2003 | |
| EP | 1 348 402 A1 | 10/2003 | |
| EP | 1 570 807 A2 | 9/2005 | |
| FR | 2 764 794 A1 | 12/1998 | |
| GB | 20200220 U1 | 4/2002 | |
| WO | 90/01969 A1 | 3/1990 | |
| WO | 90/13332 A1 | 11/1990 | |
| WO | 91/10424 A1 | 7/1991 | |
| WO | 91/11193 A1 | 8/1991 | |
| WO | 91/12779 A1 | 9/1991 | |
| WO | 92/00747 A1 | 1/1992 | |
| WO | 92/12717 A2 | 8/1992 | |
| WO | 92/15286 A1 | 9/1992 | |
| WO | 93/06792 A1 | 4/1993 | |
| WO | 93/11120 A1 | 6/1993 | |
| WO | 94/07529 A1 | 4/1994 | |
| WO | 94/13268 A1 | 6/1994 | |
| WO | 94/21308 A1 | 9/1994 | |
| WO | 94/24961 A1 | 11/1994 | |
| WO | 94/24962 A1 | 11/1994 | |
| WO | 95/03036 A1 | 2/1995 | |
| WO | 95/03795 A1 | 2/1995 | |
| WO | 95/03796 A1 | 2/1995 | |
| WO | 95/24908 A1 | 9/1995 | |
| WO | 95/25176 A1 | 9/1995 | |
| WO | 96/03092 A1 | 2/1996 | |
| WO | 96/29028 A1 | 9/1996 | |
| WO | WO 96/32907 | 10/1996 | |
| WO | 97/04721 A1 | 2/1997 | |
| WO | 97/10011 A1 | 3/1997 | |
| WO | WO 97/33534 A1 | 9/1997 | |
| WO | WO-9805270 | 2/1998 | |
| WO | 98/08566 A1 | 3/1998 | |
| WO | 98/18407 A1 | 5/1998 | |
| WO | 98/19628 A1 | 5/1998 | |
| WO | 98/23228 A1 | 6/1998 | |
| WO | 98/23244 A1 | 6/1998 | |
| WO | WO 98/23228 | 6/1998 | |
| WO | WO 98/34669 | 8/1998 | |
| WO | WO 98/36784 A | 8/1998 | |
| WO | WO 98/47447 A | 10/1998 | |
| WO | WO 98/47447 A1 | 10/1998 | |
| WO | 98/58600 A1 | 12/1998 | |
| WO | WO 98/56312 | 12/1998 | |
| WO | 99/15108 A2 | 4/1999 | |
| WO | 99/16477 A2 | 4/1999 | |
| WO | WO 99/16386 | 4/1999 | |
| WO | 99/44536 A1 | 9/1999 | |
| WO | 99/49810 A1 | 10/1999 | |
| WO | 99/49928 A1 | 10/1999 | |
| WO | 99/55395 A1 | 11/1999 | |
| WO | 00/10613 A2 | 3/2000 | |
| WO | WO-0010622 | 3/2000 | |
| WO | WO 00/21584 A1 | 4/2000 | |
| WO | WO 00/27445 A | 5/2000 | |
| WO | WO 00/32255 A | 6/2000 | |
| WO | 00/45744 A1 | 8/2000 | |
| WO | 00/71054 A1 | 11/2000 | |
| WO | WO 00/69368 | 11/2000 | |
| WO | 0117577 A1 | 3/2001 | |
| WO | 01/45763 A1 | 6/2001 | |
| WO | 01/45862 A1 | 6/2001 | |
| WO | WO-0145763 | 6/2001 | |
| WO | 01/49338 A1 | 7/2001 | |
| WO | 01/52915 A1 | 7/2001 | |
| WO | 01/87376 A1 | 11/2001 | |
| WO | WO 01/87342 A2 | 11/2001 | |
| WO | WO 01/093781 A2 | 12/2001 | |
| WO | 02/17880 A2 | 3/2002 | |
| WO | 02/26162 A2 | 4/2002 | |
| WO | WO 02/26281 A1 | 4/2002 | |
| WO | 02/41931 A2 | 5/2002 | |
| WO | WO 02/060506 A1 | 8/2002 | |
| WO | 02/087586 A1 | 11/2002 | |
| WO | WO 03/015664 A1 | 2/2003 | |
| WO | 03/018083 A2 | 3/2003 | |
| WO | WO 03/057218 A1 | 7/2003 | |
| WO | WO-2004043510 | 5/2004 | |
| WO | WO-2004043511 | 5/2004 | |
| WO | 2005/053937 A1 | 6/2005 | |
| WO | 2005/118971 A2 | 12/2005 | |
| WO | 2006/036319 A2 | 4/2006 | |

OTHER PUBLICATIONS

Serruys, Patrick W. et al., Heparin-Coated Palmaz-Schatz Stents in Human Coronary Arteries, Circulation. 1996;93:412-422.

Lundergan, Conor F., MD et al., Peptide Inhibition of Myointimal Proliferation by Angiopeptin, a Somatostatin Analogue, JACC vol. 17, No. 6, May 1991:132B-6B.

Liu, Ming Wei, MD et al., Restenosis After Coronary Angioplasty Potential Biologic Determinants and Role of Intimal Hyperplasia, Circulation 1989, 79:1374-1387.

Serruys, P. W. et al., Evaulation of Ketanserin in the Prevention of Restenosis After Percutaneous Transluminal Coronary Angioplasty—A Multicenter Randomized Double-Blind Placbo-Controlled Trial, Circulartion vol. 88, No. 4, Part 1, Oct. 1993, 1588-1601.

Berk, Bradford C. MD et al., Pharmacologic Roles of Heparin and Glucocorticoids to Prevent Restenosis After Coronary Angioplasty, JACC vol. 17, No. 6, May 1991:111B-7B.

Serruys, Patrick W. MD et al., A Comparision of Balloon-Expandable-Stent Implantation with Balloon Angioplasty in Patients with Coronary Artery Disease, The New England Journal of Medicine, vol. 331, No. 8, Aug. 25, 1994, 489-495.

Fischman, David L. MD et al., A Randomized Comparison of Coronary-Stent Placement and Balloon Angioplasty in the Treatment of Coronary Artery Disease, The New England Journal of Medicine, vol. 331, No. 8, Aug. 25, 1994, 496-501.

Colburn, Michael D. MD et al., Dose Responsive suppression of myointimal hyperlasia by dexamethasone, Journal of Vascular Surgery, vol. 15, No. 3, Mar. 1992, 510-518.

Liu Ming, W. MD, Trapidil in Preventing Restenosis After Balloon Angioplasty in the Atherosclerotic Rabbit, Circulation, vol. 81, No. 3, Mar. 1990, 1089-1093.

Hansson, Goran K. MD, et al., Interferon- Inhibits Arterial Stenosis After Injury, Circulation, vol. 84, No. 3, Sep. 1991, 1266-1272.

Snow, Alan D. et al., Heparin Modulates the Composition of th Extracellular Matrix Domain Surrounding Arterial Smooth Muscle Cells, American Journal of Pathology, vol. 137, No. 2, Aug. 1990, 313-330.

Popma, Jeffrey J. MD et al., Clinical Trials of Restenosis After Coronary Angioplasty, Circulation vol. 84, No. 3, Sep. 1991, 1426-1436.

Campbell, Gordon R. et al., Phenotypic Modulation of Smooth Muscle Cells in Primary Culture, Vascular Smooth Muscle Cells in Culture, CRC Press 1987, pp. 39-55.

Clowes, Alexander W. et al., Significance of Quiescent Smooth Muscle Migration in the Injured Rat Carotid Artery, Cir Res 56: 139-145, 1985.

Lange, Richard A. MD et al., Restenosis Ater Coronary Balloon Angioplasty, Annu. Rev. Med. 1991. 42:127-32.

Franklin, Stephen, M. MD et al., Pharmacologic prevention of restenosis after coronary angioplasty: review of the randomized clinical trials, Coronary Artery Disease, Mar. 1993, vol. 4, No. 3, 232-242.

Suppression by heparin of smooth muscle cell proliferation in injured arteries, Nature, vol. 265, Feb. 17, 1977, 625-626.

Guyton, John, R. et al., Inhibition of Rat Arterial Smooth Muscle Cell Proliferation by Heparin, Circulation Research, vol. 46, No. 5, May 1980, 625-634.

Clowes, Alexander W. et al., Kinetics of Cellular Proliferation after Arterial Injury, Circulation Research, vol. 58, No. 6, Jun. 1986, 839-845.

Majesky, Mark W., et al., Heparin Regulates Smooth Muscle S Phase Entry in the Injured Rat Carotid Artery, Circulation Research, vol. 61, No. 2, Aug. 1987, 296-300.

Okada, Tomohisa, MD et al., Localized Release of Perivascular Heparin Inhibits Intimal Proliferation after Endothelial Injury without System Anticoagulation, Neurosurgery, vol. 25, No. 6, I989, 892-898.

Vasey, Charles G, et al., Clinical Cardiology: Stress Echo and Coronary Flow, Supplement II Circulation, vol. 80, No. 4, Oct. 1989, II-66.

Powell, Jerry S. et al., Inhibitors of Angiotensin-Converting Enzyme Prevent Myointimal Proliferation After Vascular Injury, Science, vol. 245, Jul. 14, 1989, 186-188.

Jonasson, Lena et al, Cyclosporin A inhibits smooth muscle proliferation in the vascular response to injury, Proc. Natl. Acad. Sci USA 85 (1988), pp. 2303-2306.

Nemecek, Georgina M. et al., Terbinafine Inhibits the Mitogenic Response to Platelet-Derived Growth Factor in Vitro and Neointimal Proliferation in Vivo, The Journal of Pharmacology and Experimental Therapeutics, vol. 248, No. 3, 1998, 1167-1174.

Siekierka, John J., Probing T-Cell Signal Transduction Pathways with the Immunosuppressive Drugs, FK-506 and Rapamycin, Immunologic Research 1994, 13:110-116.

Poon, Michael et al., Rapamycin Inhibits Vascular Smooth Muscle Cell Migration, J. Clin. Invest., vol. 98, No. 10, Nov. 1996, 2277-2283.

Gregory, Clare R. et al., Rapamycin Inhibits Arterial Intimal Thickening Caused by Both Alloimmune and Mechanical Injury, Transplantation vol. 55, No. 6, Jun. 1993, 1409-1418.

European Search Report dated Jun. 10, 2008 corresponding to Application No. EP07001395.8.

Canadian Search Report dated May 27, 2008 corresponding to Application No. 2,424,305.

Canadian Search Report dated Mar. 19, 2009 corresponding to Application No. 2,424,305.

Grayson, A.C. Richards e t al., "Multi-pulse Drug Delivery From a Resorbable Polymeric Microchip Device", Nature Materials, vol. 2, Nov. 2003, pp. 767-770.

Hakan, E. et al., The Jostent Coronary Stent Range, Ch. 19.

Hiatt, B.L. et al., "The Drug-Eluting Stent: Is it the Holy Grail?" Reviews in Cardiovascular medicine, 2001, vol. 2, No. 4, pp. 190-196.

Hwang, C. et al., "*Physiological Transport forces Govern Drug Distribution for Stent-Based Delivery*", Circulation, 104, 2001, pp. 600-605.

Kornowski, R. et al., "Slow-Release Taxol coated GR11 Stents Reduce Neointima Formation in a Porcine Coronary in Stent Restenosis Model" Abstract from the American Hear Associatiion's 70th Scientific Sessions, Nov. 9-12, 1997.

Reifart, Nicholas, "*The Jostent Coronary Stent Range*," Chapt. 16, JOMED AB, Helsingborg, Sweden, Handbook of Coronary Stents.

West, J.L., *Drug Delivery—Pulsed Polymers*, Materials, vol. 2, Nov. 2003, pp. 709-710.

* cited by examiner

EXPANDABLE MEDICAL DEVICE WITH BENEFICIAL AGENT DELIVERY MECHANISM

This application is a continuation divisional of application Ser. No. 09/649,217, filed on Aug. 28, 2000 now U.S. Pat. No. 6,562,065, which is a continuation of application Ser. No. 09/183,555, filed on Oct. 29, 1998, now U.S. Pat. No. 6,241,762, which claims priority to Provisional Application No. 60/079,881 filed on Mar. 30, 1998.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665, 4,739,762, and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. The force required to expand these tubular stents is proportional to the thickness of the wall material in a radial direction. To keep expansion forces within acceptable levels for use within the body (e.g., 5-10 atm), these designs must use very thin-walled materials (e.g., stainless steel tubing with 0.0025 inch thick walls). However, materials this thin are not visible on conventional fluoroscopic and x-ray equipment and it is therefore difficult to place the stents accurately or to find and retrieve stents that subsequently become dislodged and lost in the circulatory system.

Further, many of these thin-walled tubular stent designs employ networks of long, slender struts whose width in a circumferential direction is two or more times greater than their thickness in a radial direction. When expanded, these struts are frequently unstable, that is, they display a tendency to buckle, with individual struts twisting out of plane. Excessive protrusion of these twisted struts into the bloodstream has been observed to increase turbulence, and thus encourage thrombosis. Additional procedures have often been required to attempt to correct this problem of buckled struts. For example, after initial stent implantation is determined to have caused buckling of struts, a second, high-pressure balloon (e.g., 12 to 18 atm) would be used to attempt to drive the twisted struts further into the lumen wall. These secondary procedures can be dangerous to the patient due to the risk of collateral damage to the lumen wall.

Many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue. Known stents of the type described above experience recoil of up to about 6 to 12% from maximum expansion.

Large recoil also makes it very difficult to securely crimp most known stents onto delivery catheter balloons. As a result, slippage of stents on balloons during interlumenal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Another problem with known stent designs is non-uniformity in the geometry of the expanded stent. Non-uniform expansion can lead to non-uniform coverage of the lumen wall creating gaps in coverage and inadequate lumen support. Further, over expansion in some regions or cells of the stent can lead to excessive material strain and even failure of stent features. This problem is potentially worse in low expansion force stents having smaller feature widths and thicknesses in which manufacturing variations become proportionately more significant. In addition, a typical delivery catheter for use in expanding a stent includes a balloon folded into a compact shape for catheter insertion. The balloon is expanded by fluid pressure to unfold the balloon and deploy the stent. This process of unfolding the balloon causes uneven stresses to be applied to the stent during expansion of the balloon due to the folds causing the problem non-uniform stent expansion.

U.S. Pat. No. 5,545,210 discloses a thin-walled tubular stent geometrically similar to those discussed above, but constructed of a nickel-titanium shape memory alloy ("Nitinol"). This design permits the use of cylinders with thicker walls by making use of the lower yield stress and lower elastic modulus of martensitic phase Nitinol alloys. The expansion force required to expand a Nitinol stent is less than that of comparable thickness stainless steel stents of a conventional design. However, the "recoil" problem after expansion is significantly greater with Nitinol than with other materials. For example, recoil of a typical design Nitinol stent is about 9%. Nitinol is also more expensive, and more difficult to fabricate and machine than other stent materials, such as stainless steel.

All of the above stents share a critical design property: in each design, the features that undergo permanent deformation during stent expansion are prismatic, i.e., the cross sections of these features remain constant or change very gradually along their entire active length. To a first approximation, such features deform under transverse stress as simple beams with fixed or guided ends: essentially, the features act as a leaf springs. These leaf spring like structures are ideally suited to providing large amounts of elastic deformation before permanent deformation commences. This is exactly the opposite of ideal stent behavior. Further, the force required to deflect prismatic stent struts in the circumferential direction during stent expansion is proportional to the square of the width of the strut in the circumferential direction. Expansion forces thus increase rapidly with strut width in the above stent designs. Typical expansion pressures required to expand known stents are between about 5 and 10 atmospheres. These forces can cause substantial damage to tissue if misapplied.

FIG. 1 shows a typical prior art "expanding cage" stent design. The stent 10 includes a series of axial slots 12 formed in a cylindrical tube 14. Each axial row of slots 12 is displaced axially from the adjacent row by approximately half the slot length providing a staggered slot arrangement. The material between the slots 12 forms a network of axial struts 16 joined by short circumferential links 18. The cross section of each strut 16 remains constant or varies gradually along the entire length of the strut and thus the rectangular moment of inertia and the elastic and plastic section module of the cross section also remain constant or vary gradually along the length of the strut. Such a strut 16 is commonly referred to as a prismatic beam. Struts 16 in this type of design are typically 0.005 to 0.006 inches (0.127-0.1524 mm) wide in the circumferential direction. Strut thicknesses in the radial direction are typically about 0.0025 inches (0.0635 mm) or less to keep expansion forces within acceptable levels. However, most stent materials must be approximately 0.005 inches (0.127 mm) thick for good visibility on conventional fluoroscopic equipment. This high ratio of strut width to thickness, combined with the relatively high strut length and the initial curvature of the stent tubing combine to cause the instability and bucking often seen in this type of stent design. When expanded, the stent structure of FIG. 1 assumes the roughly diamond pattern commonly seen in expanded sheet metal.

Another stent described in PCT publication number WO 96/29028 uses struts with relatively weak portions of locally-reduced cross sections which on expansion of the stent act to concentrate deformation at these areas. However, as discussed above non-uniform expansion is even more of a problem when smaller feature widths and thicknesses are involved because manufacturing variations become proportionately more significant. The locally-reduced cross section portions described in this document are formed by pairs of circular holes. The shape of the locally-reduced cross section portions undesirably concentrates the plastic strain at the narrowest portion. This concentration of plastic strain without any provision for controlling the level of plastic strain makes the stent highly vulnerable to failure.

In view of the drawbacks of the prior art stents, it would be advantageous to be able to expand a stent with an expansion force at a low level independent of choice of stent materials, material thickness, or strut dimensions.

It would farther be advantageous to have a tissue-supporting device that permits a choice of material thickness that could be viewed easily on conventional fluoroscopic equipment for any material.

It would also be advantageous to have a tissue-supporting device that is inherently stable during expansion, thus eliminating buckling and twisting of structural features during stent deployment.

It would also be desirable to control strain to a desired level which takes advantage of work hardening without approaching a level of plastic strain at which failure may occur.

In addition, it would be advantageous to have a tissue-supporting device with minimal elastic recovery, or "recoil" of the device after expansion.

It would be advantageous to have a tissue supporting device that can be securely crimped to the delivery catheter without requiring special tools, techniques, or ancillary clamping features.

It would further be advantageous to have a tissue-supporting device that has improved resistance to compressive forces (improved crush strength) after expansion.

It would also be advantageous to have a tissue-supporting device that achieves all the above improvements with minimal foreshortening of the overall stent length during expansion.

SUMMARY OF THE INVENTION

The present invention addresses several important problems in expandable medical device design including: high expansion force requirements; lack of radio-opacity in thin-walled stents; buckling and twisting of stent features during expansion; poor crimping properties; and excessive elastic recovery ("recoil") after implantation. The invention also provides benefits of improved resistance to compressive forces-after expansion, control of the level of plastic strain, and low axial shortening during expansion. Some embodiments of the invention also provide improved uniformity of expansion by limiting a maximum geometric deflection between struts. The invention may also incorporate sites for the inclusion of beneficial agent delivery.

The invention involves the incorporation of stress/strain concentration features or "ductile hinges" at selected points in the body of an expandable cylindrical medical device. When expansion forces are applied to the device as a whole, these ductile hinges concentrate expansion stresses and strains in small, well-defined areas while limiting strut deflection and plastic strain to specified levels.

In accordance with one aspect of the present invention, an expandable medical device includes a plurality of elongated beams having a substantially constant beam cross sectional area along a beam length. The plurality of elongated beams are joined together to form a substantially cylindrical device which is expandable from a cylinder having a first diameter to a cylinder having a second diameter. A plurality of ductile hinges connect the plurality of beams together in the substantially cylindrical device. The ductile hinges have a substantially constant hinge cross sectional area along a substantial portion of a hinge length. The hinge cross sectional area is smaller than the beam cross sectional area such that as the device is expanded from the first diameter to the second diameter the ductile hinges experience plastic deformation while the beams are not plastically deformed.

In accordance with a further aspect of the invention, an expandable medical device includes a cylindrical tube, and a plurality of axial slots formed in the cylindrical tube in a staggered arrangement to define a network of elongated struts, wherein each of the elongated struts are axially displaced from adjacent struts. A plurality of ductile hinges are formed between the elongated struts. The ductile hinges allow the cylindrical tube to be expanded or compressed from a first diameter to a second diameter by deformation of the ductile hinges. The ductile hinges are asymmetrically configured to reach a predetermined strain level upon a first percentage expansion and to reach the predetermined strain level upon a second percentage of compression, wherein the first percentage is larger than the second percentage.

In accordance with another aspect of the present invention, an expandable medical device includes a plurality of elongated beams having a substantially constant beam cross sectional area along a beam length. A plurality of ductile hinges connect the plurality of beams together in a substantially cylindrical device which is expandable or compressible from a first diameter to a second diameter by plastic deformation of the ductile hinges. A plurality of deflection limiting members are positioned at a plurality of the ductile hinges which limit the deflection at the ductile hinges.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
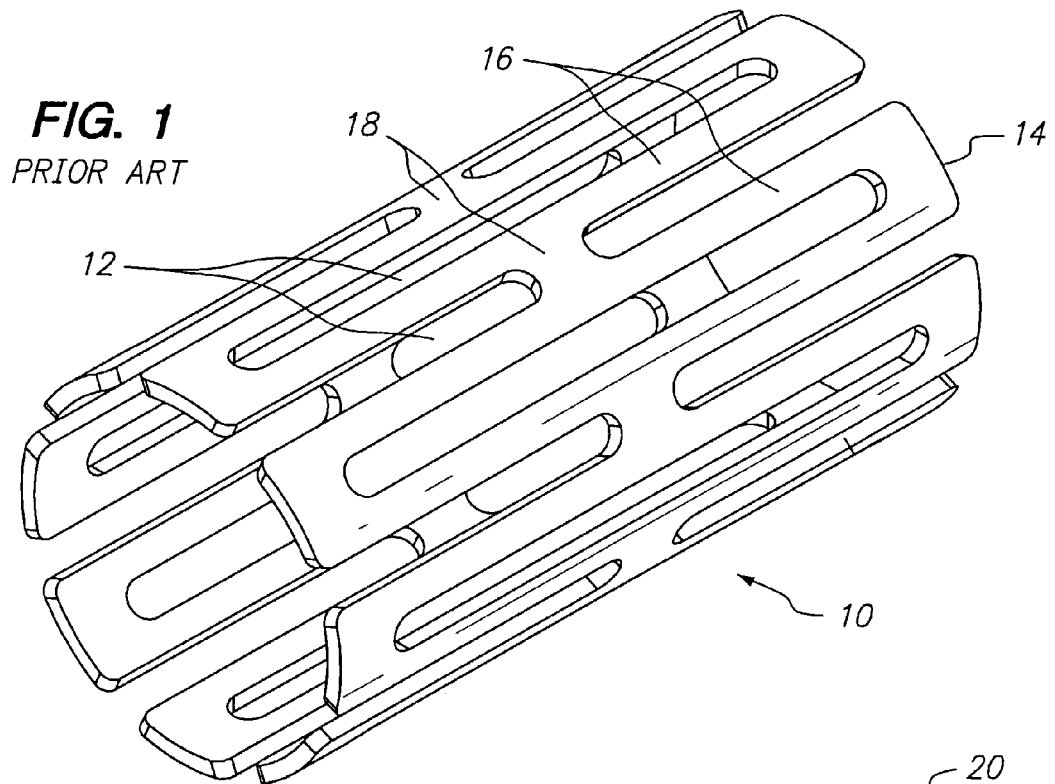
FIG. 1 is an isometric view of a prior art tissue-supporting device.
Figure 2:
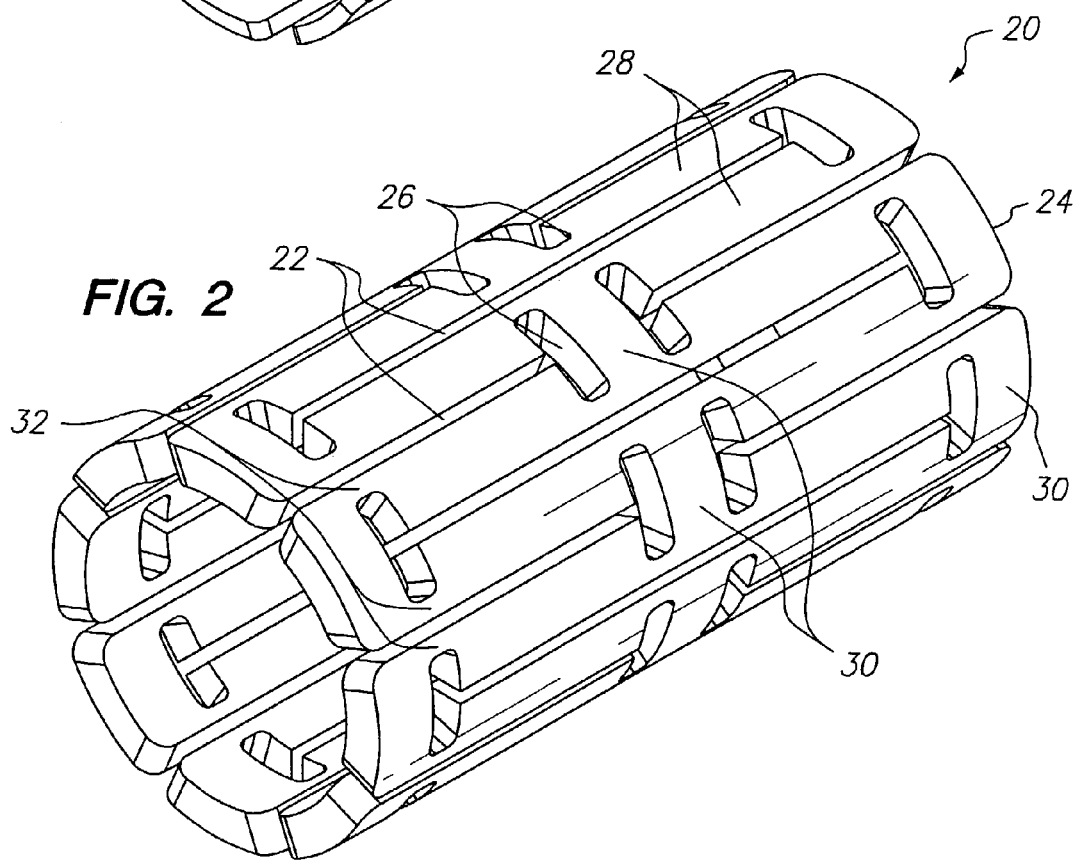
FIG. 2 is an isometric view of a tissue-supporting device in accordance with one embodiment of the invention.

FIG. 2 shows one embodiment of an expandable tissue supporting device 20 in accordance with the present invention. The tissue supporting device 20 includes a series of axial slots 22 formed in a cylindrical tube 24. Each axial slot 22 is displaced axially from the slots in adjacent rows of slots by approximately half the slot length resulting in a staggered slot arrangement. The offset between adjacent rows of slots results in alternate rows of slots which extend to the ends of the cylindrical tube 24. At each interior end of each of the axial slots 22 a circumferential slot 26 is formed. The material between the slots 22 forms a network of axial struts 28 extending substantially parallel to an axis of the tube 24. The axial struts 28 are joined by short circumferential links 30. The circumferential links 30 are positioned at both the interior of the cylindrical tube and at the ends of the cylindrical tube. The cross section (and rectangular moment of inertia) of each of the struts 28 is not constant along the length of the strut. Rather, the strut cross section changes abruptly at both ends of each strut 28 at the location of the circumferential slots 26. The struts 28 are thus not prismatic. Each individual strut 28 is linked to the rest of the structure through a pair of reduced sections 32, one at each end, which act as stress/strain concentration features. The reduced sections 32 of the struts function as hinges in the cylindrical structure. Since the stress/strain concentration features 32 are designed to operate into the plastic deformation range of generally ductile materials, they are referred to as ductile hinges. Such features are also commonly referred to as "Notch Hinges" or "Notch Springs" in ultra-precision mechanism design, where they are used exclusively in the elastic range:

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

The presence of the ductile hinges 32 allows all of the remaining features in the tissue supporting device to be increased in width or the circumferentially oriented component of their respective rectangular moments of inertia—thus greatly increasing the strength and rigidity of these features. The net result is that elastic, and then plastic deformation commence and propagate in the ductile hinges 32 before other structural elements of the device undergo any significant elastic deformation. The force required to expand the tissue supporting device 20 becomes a function of the geometry of the ductile hinges 32, rather than the device structure as a whole, and arbitrarily small expansion forces, can be specified by changing hinge geometry for virtually any material wall thickness. In particular, wall thicknesses great enough to be visible on a fluoroscope can be chosen for any material of interest.

In order to get minimum recoil, the ductile hinges 32 should be designed to operate well into the plastic range of the material, and relatively high local strain-curvatures are developed. When these conditions apply, elastic curvature is a very small fraction of plastic or total curvature, and thus when expansion forces are relaxed, the percent change in hinge curvature is very small. When incorporated into a strut network designed to take maximum advantage of this effect, the elastic springback, or "recoil," of the overall stent structure is minimized.

In the embodiment of FIG. 2, it is desirable to increase the width of the individual struts 28 between the ductile hinges 32 to the maximum width that is geometrically possible for a given diameter and a given number of struts arrayed around that diameter. The only geometric limitation on strut width is the minimum practical width of the slots 22 which is about 0.002 inches (0.0508 mm) for laser machining. Lateral stiffness of the struts 28 increases as the cube of strut width, so that relatively small increases in strut width significantly increase strut stiffness. The net result of inserting ductile hinges 32 and increasing strut width is that the struts 28 no longer act as flexible leaf springs, but act as essentially rigid beams between the ductile hinges. All radial expansion or compression of the cylindrical tissue supporting device 20 is accommodated by mechanical strain in the hinge features 32, and yield in the hinge commences at very small overall radial expansion or compression.

Yield in ductile hinges at very low gross radial deflections also provides the superior crimping properties displayed by the ductile hinge-based designs. When a tissue supporting device is crimped onto a folded catheter balloon, very little radial compression of the device is possible since the initial fit between balloon and device is already snug. Most stents simply rebound elastically after such compression, resulting in very low clamping forces and the attendant tendency for the stent to slip on the balloon. Ductile hinges, however, sustain significant plastic deformation even at the low deflections occurring during crimping onto the balloon, and therefore a device employing ductile hinges displays much higher clamping forces. The ductile hinge designs according to the present invention may be securely crimped onto a balloon of a delivery catheter by hand or by machine without the need for auxiliary retaining devices commonly used to hold known stents in place.

The geometric details of the stress/strain concentration features or ductile hinges 32 can be varied greatly to tailor the exact mechanical expansion properties to those required in a specific application. The most obvious and straightforward ductile hinges are formed by slots or notches with rounded roots, as in FIGS. 3a and 3c. Since the laser beams often used to fabricate these features are themselves round, slots or notches with circular roots are also among the easiest to fabricate.

Figure 3A:
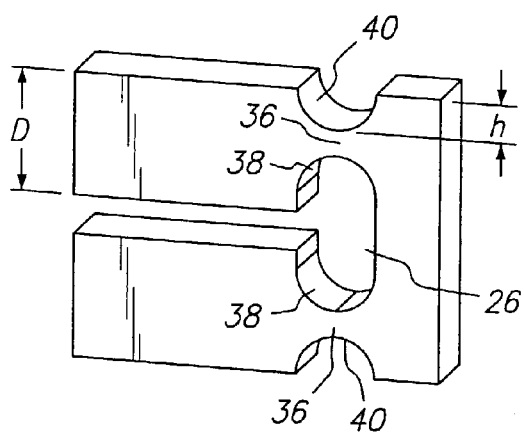
FIGS. 3a-d are perspective views of ductile hinges according to several variations of the invention.

FIG. 3a shows a ductile hinge 36 formed by a pair of opposed circular grooves 38, 40. According to this embodiment the circumferential slot 26 has semicircular ends 38 having a radius of curvature. Outer semicircular grooves 40 oppose the semicircular ends 38 and also have a radius of curvature which is the same as that of the grooves 38. FIG. 3c shows another ductile hinge 54 formed by a parabolic groove 56.

Generally, the ductile hinges 36 of the embodiment of FIG. 3a formed between pairs of concave curves 38, 40 have a minimum width along a line connecting their respective centers of curvature. When the struts connected by the ductile hinge are moved apart or together, plastic deformation is highly concentrated in a region immediately adjacent to the plane that bisects the hinge at this narrow point.

For smaller deflection, this very high strain concentration at the bisecting plane is acceptable, and in some cases, useful. For stent crimping purposes, for example, it is desirable to generate relatively large plastic deformations at very small deflection angles.

As a practical matter, however, strut deflection angles for device expansion are often in the 25° to 45° range. At these angles, strain at the root or bisecting plane of concave ductile hinge features can easily exceed the 50 to 60% elongation-to-failure of 316L stainless steel, one of the most ductile stent materials. Deflection limiting features which will be described further below limit the geometric deflection of struts, but these features do not in themselves affect the propagation pattern of plastic deformation in a given ductile hinge design. For concave ductile hinges at large bend angles, very high strain concentrations remain. Scanning electron micrographs have confirmed this analysis.

In many engineering applications, it is desirable to limit the amount of strain, or "cold-work," in a material to a specified level in order to optimize material properties and to assure safe operation. For example, in medical applications it is desirable to limit the amount of cold-work in 316L stainless steel to about 30%. At this level, the strength of the material is increased, while the material strain is still well below the failure range. Ideally, therefore, a safe and effective ductile hinge should not simply limit gross deflection, but reliably limit material strain to a specified level.

Figure 3B:
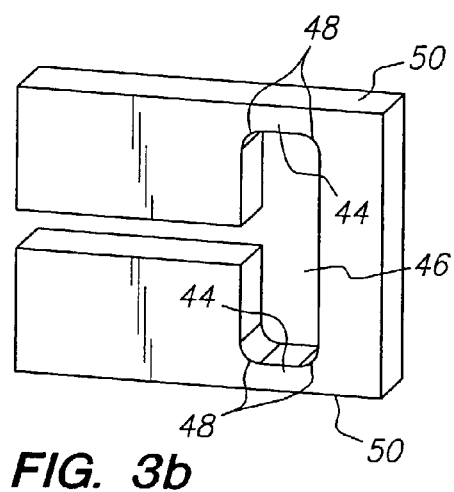
Figure 3C:
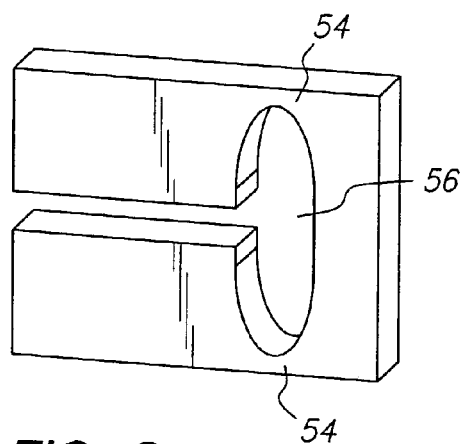

FIG. 3b shows a simple ductile hinge design that allows material strain to be limited to some specified level. The ductile hinge of FIG. 3b is formed by a rectangular circumferential groove 46 with filleted corners 48 on one side of a strut, the opposite side 50 of the strut remaining straight. The ductile hinges 44 are substantially rectangular sections between the ends of the groove 46 and the side walls 50.

One of the key concepts in FIG. 3b is that the ductile hinge 44 has a constant or substantially constant width along at least a portion of its total length. In this configuration, there is no local minimum width along the ductile hinge axis, as there is with pairs of concave roots. There is therefore no point concentration of stresses and strains along the length of the ductile hinge beam during stent expansion. In particular, maximum tensile and compressive strains will be distributed evenly along the upper and lower surfaces of the hinge 44 during stent expansion. With the gross bend angle limited by mechanical stops, which are described below in detail, the maximum material strain (at the hinge surfaces) can therefore be reliably limited by adjusting the initial length of the ductile hinge over which the total elongation is distributed.

Figure 3D:
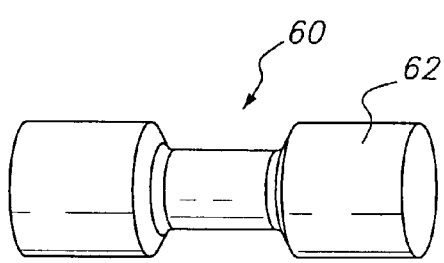

FIG. 3d shows a ductile hinge 60 in a cylindrical wire 62 for incorporating into a wire-form tissue-supporting device. The ductile hinge 60 is formed by a reduced diameter portion of the wire 62. Again, it is important that the ductile hinge have a substantially constant width over a portion of its length in order to provide strain control. Preferably, the ductile hinge is prismatic over a portion of its length. Maximum material strain can be varied by adjusting the hinge length. The ductile hinges of the present invention have a constant or substantially constant width over at least ⅓ of the ductile hinge length, and preferably over at least ½ of the ductile hinge length.

Figure 3E:
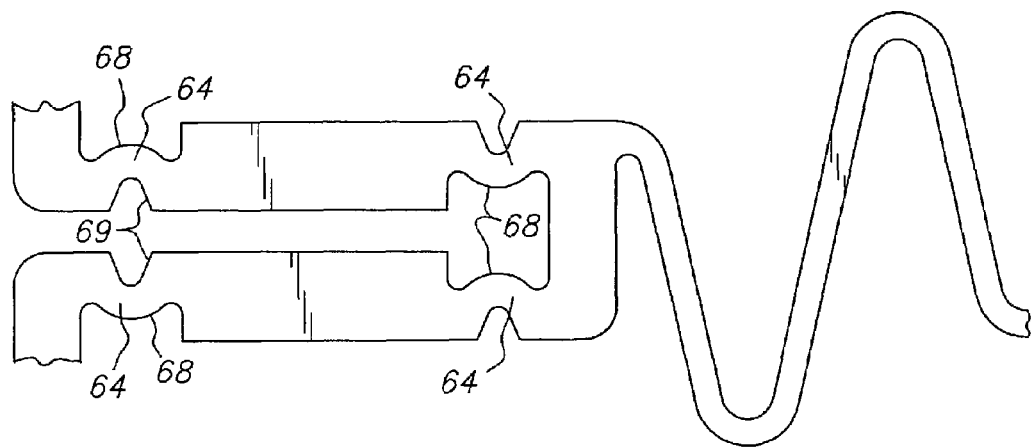
FIG. 3e is a side view of another embodiment of a ductile hinge.

FIG. 3e shows an asymmetric ductile hinge 64 that produces different strain versus deflection-angle functions in expansion and compression. Each of the ductile hinges 64 is formed between a convex surface 68 and a concave surface 69. The ductile hinge 64 according to a preferred embodiment essentially takes the form of a small, prismatic curved beam having a substantially constant cross section. However, a thickness of the curved ductile hinge 64 may vary somewhat as long as the ductile hinge width remains constant along a portion of the hinge length. The width of the curved beam is measured along the radius of curvature of the beam. This small curved beam is oriented such that the small concave surface 69 is placed in tension in the device crimping direction, while the larger convex surface 68 of the ductile hinges is placed in tension in the device expansion direction. Again, there is no local minimum width of the ductile hinge 64 along the (curved) ductile hinge axis, and no concentration of material strain. During device expansion tensile strain will be distributed along the convex surface 68 of the hinge 64 and maximum expansion will be limited by the angle of the walls of the concave notch 69 which provide a geometric deflection limiting feature. Maximum tensile strain can therefore be reliably limited by adjusting the initial length of the convex arc shaped ductile hinge 64 over which the total elongation is distributed.

The ductile hinges illustrated in FIGS. 3a-e are examples of different structures that will function as a stress/strain concentrator. Many other stress/strain concentrator configurations may also be used as the ductile hinges in the present invention. The ductile hinges according to the present invention generally include an abrupt change in width of a strut that functions to concentrate stresses and strains in the narrower section of the strut. These ductile hinges also generally include features to limit mechanical deflection of attached struts and features to control material strain during large strut deflections. Although the ductile hinges have been illustrated in FIG. 2 as positioned at the ends of each of the axial slots 22, they may also be positioned at other locations in other designs without departing from the present invention.

Figure 4A:
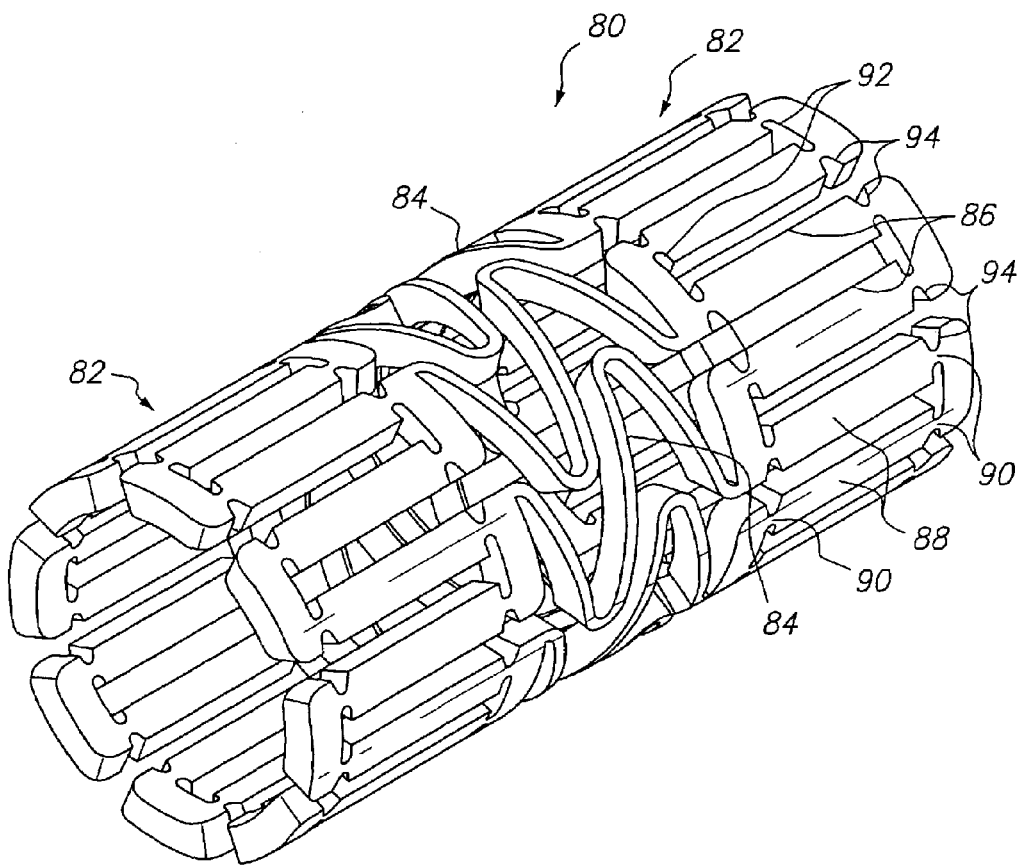
FIGS. 4a and 4b are an isometric view and an enlarged side view of a tissue-supporting device in accordance with an alternative embodiment of the invention.
Figure 4B:
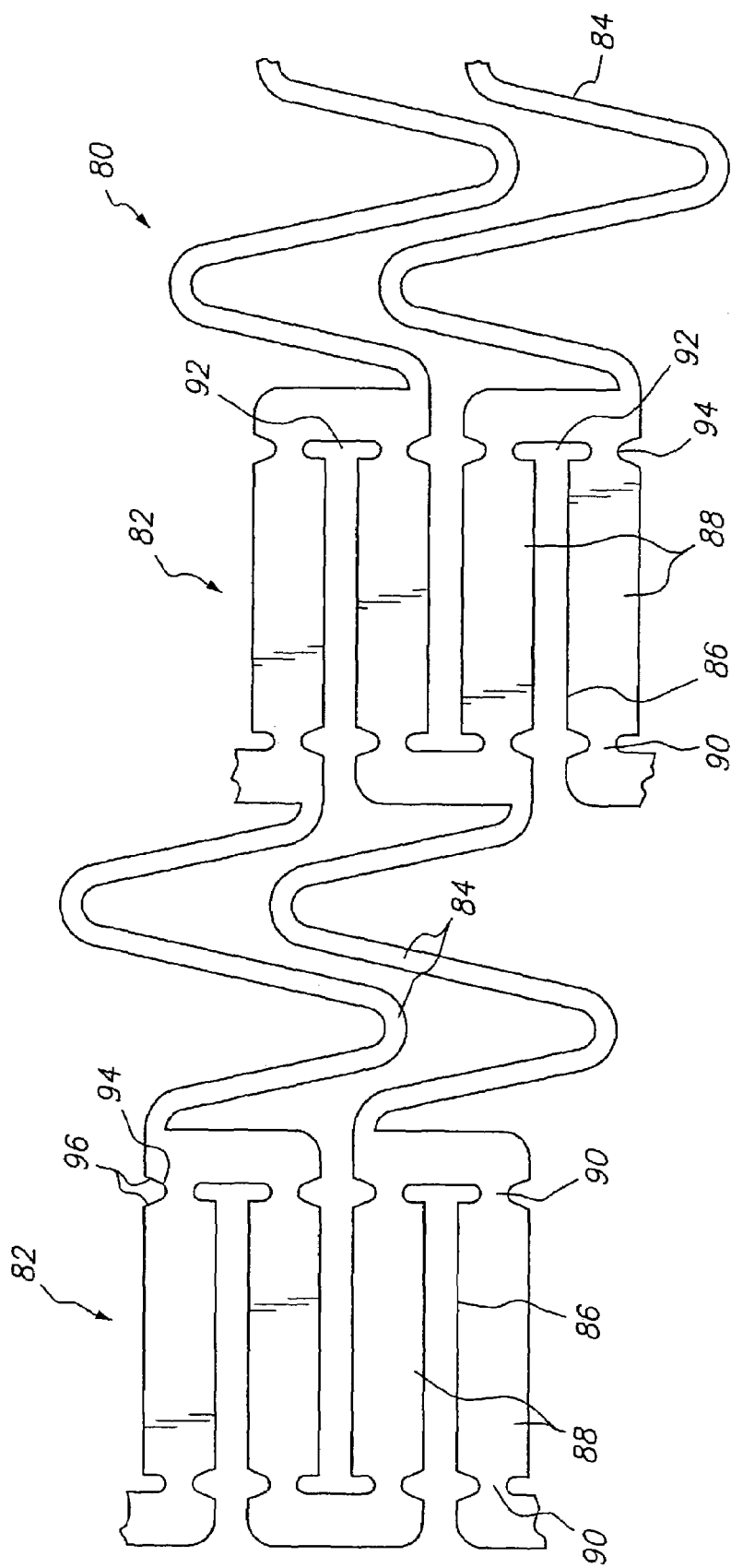

An alternative embodiment of a tissue supporting device 80 is illustrated in FIG. 4a and in the enlarged side view of FIG. 4b. The tissue supporting device 80 includes a plurality of cylindrical tubes 82 connected by S-shaped bridging elements 84. The bridging elements 84 allow the tissue supporting device to bend axially when passing through the tortuous path of the vasculature to the deployment site and allow the device to bend when necessary to match the curvature of a lumen to be supported. The S-shaped bridging elements 84 provide improved axial flexibility over prior art devices due to the thickness of the elements in the radial direction which allows the width of the elements to be relatively small without sacrificing radial strength. For example, the width of the bridging elements 84 may be about 0.0012-0.0013 inches (0.0305-0.0330 mm). Each of the cylindrical tubes 82 has a plurality of axial slots 86 extending from an end surface of the cylindrical tube toward an opposite end surface. A plurality of axial struts 88 having ductile hinges 90 are formed between the axial slots 86. The ductile hinges 90 are formed by circumferential slots 92 formed at the interior ends of the axial slots 86 and opposed notches 94.

The notches 94 each have two opposed angled walls 96 which function as a stop to limit geometric deflection of the ductile hinge, and thus limit maximum device expansion. As the cylindrical tubes 82 are expanded and bending occurs at the ductile hinges 90, the angled side walls 96 of the notches 94 move toward each other. Once the opposite side walls 96 of a notch come into contact with each other, they resist further expansion of the particular ductile hinge causing further expansion to occur at other sections of the tissue supporting device. This geometric deflection limiting feature is particularly useful where uneven expansion is caused by either variations in the tissue supporting device 80 due to manufacturing tolerances or uneven balloon expansion.

The tissue supporting device 20, 80 according to the present invention may be formed of any ductile material, such as steel, gold, silver, tantalum, titanium, Nitinol, other shape memory alloys, other metals, or even some plastics. One preferred method for making the tissue supporting device 20, 80 involves forming a cylindrical tube and then laser cutting the slots 22, 26, 86, 92 and notches 94 into the tube. Alternatively, the tissue supporting device may be formed by electromachining, chemical etching followed by rolling and welding, or any other known method.

The design and analysis of stress/strain concentration for ductile hinges, and stress/strain concentration features in general, is complex. For example, the stress concentration factor for the simplified ductile hinge geometry of FIG. 3a can be calculated and is given by the following expression where D is the width of the struts 28, h is the height of the circular grooves 38, 40, and r is the radius of curvature of the grooves. For purposes of this example the ratio of h/r is taken to be 4. However, other ratios of h/r can also be implemented successfully.

$$K = 4.935 - 7.586\left(\frac{2h}{D}\right) + 0.515\left(\frac{2h}{D}\right)^2 + 0.432\left(\frac{2h}{D}\right)^3$$

The stress concentration factors are generally useful only in the linear elastic range. Stress concentration patterns for a number of other geometries can be determined through photoelastic measurements and other experimental methods. Stent designs based on the use of stress/strain concentration features, or ductile hinges, generally involve more complex hinge geometries and operate in the non-linear elastic and plastic deformation regimes.

Figure 5A:
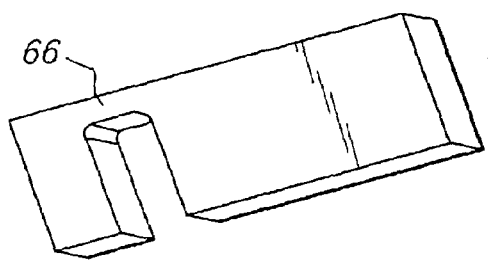
FIGS. 5a-c are perspective, side, and cross-sectional views of an idealized ductile hinge for purposes of analysis.
Figure 5B:
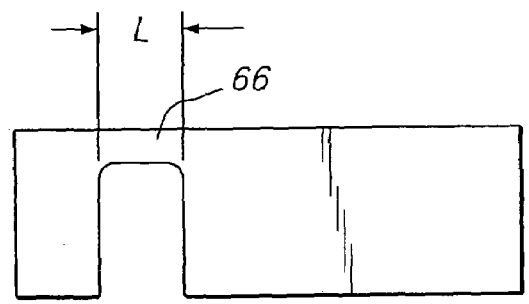
Figure 5C:
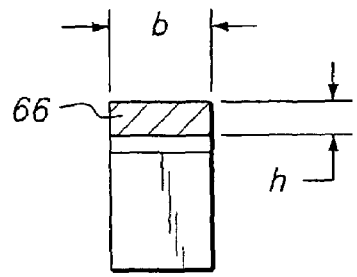
Figure 5D:
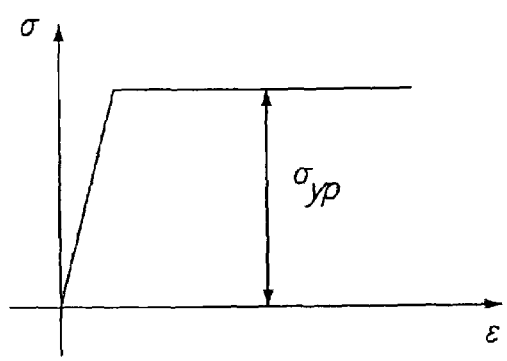
FIG. 5d is a stress/strain curve for the idealized ductile hinge.

The general nature of the relationship among applied forces, material properties, and ductile hinge geometry can be more easily understood through analysis of an idealized hinge 66 as shown in FIGS. 5a-5c. The hinge 66 is a simple beam of rectangular cross section having a width h, length L and thickness b. The idealized hinge 66 has elastic-ideally-plastic material properties which are characterized by the ideal stress/strain curve of FIG. 5d. It can be shown that the "plastic" or "ultimate bending moment" for such a beam is given by the expression:

$$M_p \equiv M_{ult} = \delta_{yp}\frac{bh^2}{4}$$

Where b corresponds to the cylindrical tube wall thickness, h is the circumferential width of the ductile hinge, and $\delta_{yp}$ is the yield stress of the hinge material. Assuming only that expansion pressure is proportional to the plastic moment, it can be seen that the required expansion pressure to expand the tissue supporting device increases linearly with wall thickness b and as the square of ductile hinge width h. It is thus possible to compensate for relatively large changes in wall thickness b with relatively small changes in hinge width h. While the above idealized case is only approximate, empirical measurements of expansion forces for different hinge widths in several different ductile hinge geometries have confirmed the general form of this relationship. Accordingly, for different ductile hinge geometries it is possible to increase the thickness of the tissue supporting device to achieve radiopacity while compensating for the increased thickness with a much smaller decrease in hinge width.

Ideally, the stent wall thickness b should be as thin as possible while still providing good visibility on a fluoroscope. For most stent materials, including stainless steel, this would suggest a thickness of about 0.005-0.007 inches (0.127-0.178 mm) or greater. The inclusion of ductile hinges in a stent design can lower expansion forces/pressures to very low levels for any material thickness of interest. Thus ductile hinges allow the construction of optimal wall thickness tissue supporting devices at expansion force levels significantly lower than current non-visible designs.

The expansion forces required to expand the tissue supporting device 20 according to the present invention from an initial condition illustrated in FIG. 2 to an expanded condition is between 1 and 5 atmospheres, preferably between 2 and 3 atmospheres. The expansion may be performed in a known manner, such as by inflation of a balloon or by a mandrel. The tissue supporting device 20 in the expanded condition has a diameter which is preferably up to three times the diameter of the device in the initial unexpanded condition.

Figure 6:
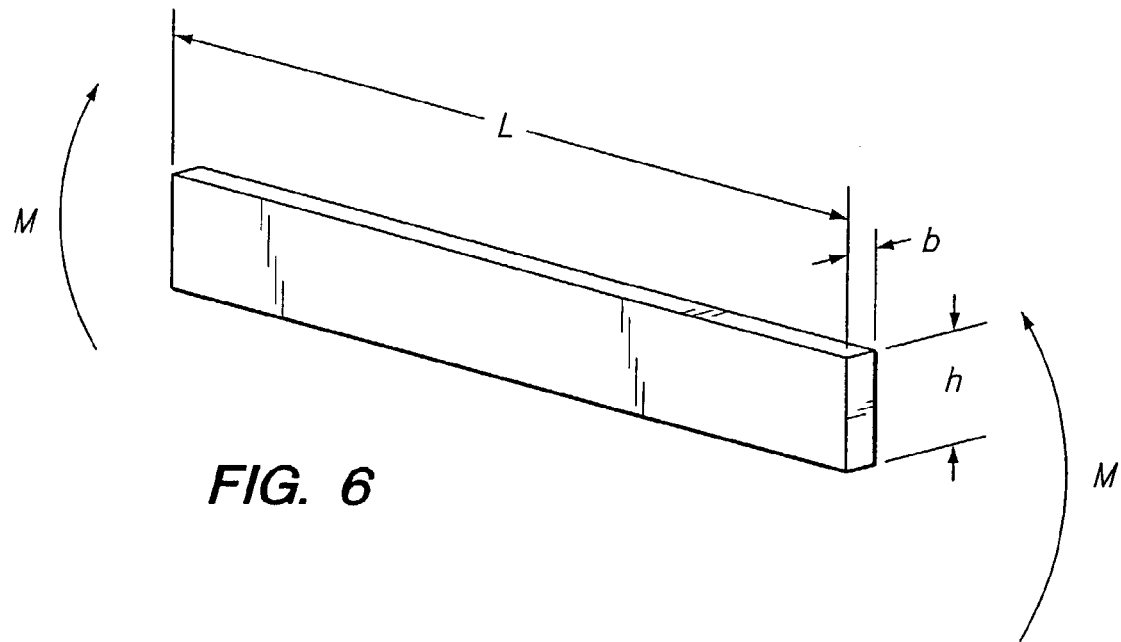
FIG. 6 is a perspective view of a simple beam for purposes of calculation.

Many tissue supporting devices fashioned from cylindrical tubes comprise networks of long, narrow, prismatic beams of essentially rectangular cross section as shown in FIG. 6. These beams which make up the known tissue supporting devices may be straight or curved, depending on the particular design. Known expandable tissue supporting devices have a typical wall thickness b of 0.0025 inches (0.0635 mm), and a typical strut width h of 0.005 to 0.006 inches (0.127-0.1524 mm). The ratio of b:h for most known designs is 1:2 or lower. As b decreases and as the beam length L increases, the beam is increasingly likely to respond to an applied bending moment M by buckling, and many designs of the prior art have displayed this behavior. This can be seen in the following expression for the "critical buckling moment" for the beam of FIG. 6.

$$M_{crit} = \frac{\pi b^3 h\sqrt{EG(1 - 0.63b/h)}}{6L}$$

Where
E=Modulus of Elasticity
G=Shear Modulus

By contrast, in a ductile hinge based design according to the present invention, only the hinge itself deforms during expansion. The typical ductile hinge 32 is not a long narrow beam as are the struts in the known stents. Wall thickness of the present invention may be increased to 0.005 inches (0.127 mm) or greater, while hinge width is typically 0.002-0.003 inches (0.0508-0.0762 mm), preferably 0.0025 inches (0.0635 mm) or less. Typical hinge length, at 0.002 to 0.005 inches (0.0508-0.0127 mm), is more than an order of magnitude less than typical strut length. Thus, the ratio of b:h in a typical ductile hinge 32 is 2:1 or greater. This is an inherently stable ratio, meaning that the plastic moment for such a ductile hinge beam is much lower than the critical buckling moment $M_{crit}$, and the ductile hinge beam deforms through-normal strain-curvature. Ductile hinges 32 are thus not vulnerable to buckling when subjected to bending moments during expansion of the tissue supporting device 20.

To provide optimal recoil and crush-strength properties, it is desirable to design the ductile hinges so that relatively large strains, and thus large curvatures, are imparted to the hinge during expansion of the tissue supporting device. Curvature is defined as the reciprocal of the radius of curvature of the neutral axis of a beam in pure bending. A larger curvature during expansion results in the elastic curvature of the hinge being a small fraction of the total hinge curvature. Thus, the gross elastic recoil of the tissue supporting device is a small fraction of the total change in circumference. It is generally possible to do this because common stent materials, such as 316L Stainless Steel have very large elongations-to-failure (i.e., they are very ductile).

It is not practical to derive exact expressions for residual curvatures for complex hinge geometries and real materials (i.e., materials with non-idealized stress/strain curves). The general nature of residual curvatures and recoil of a ductile hinge may be understood by examining the moment-curvature relationship for the elastic-ideally-plastic rectangular hinge 66 shown in FIGS. 5a-c. It may be shown that the relationship between the applied moment and the resulting beam curvature is:

$$M = M_P\left[1 - 1/3\left(\frac{y_o}{h/2}\right)^2\right] = 3/2 M_{yp}\left[1 - 1/3\left(\frac{\kappa_{yp}}{\kappa}\right)^2\right]$$

Figure 7:
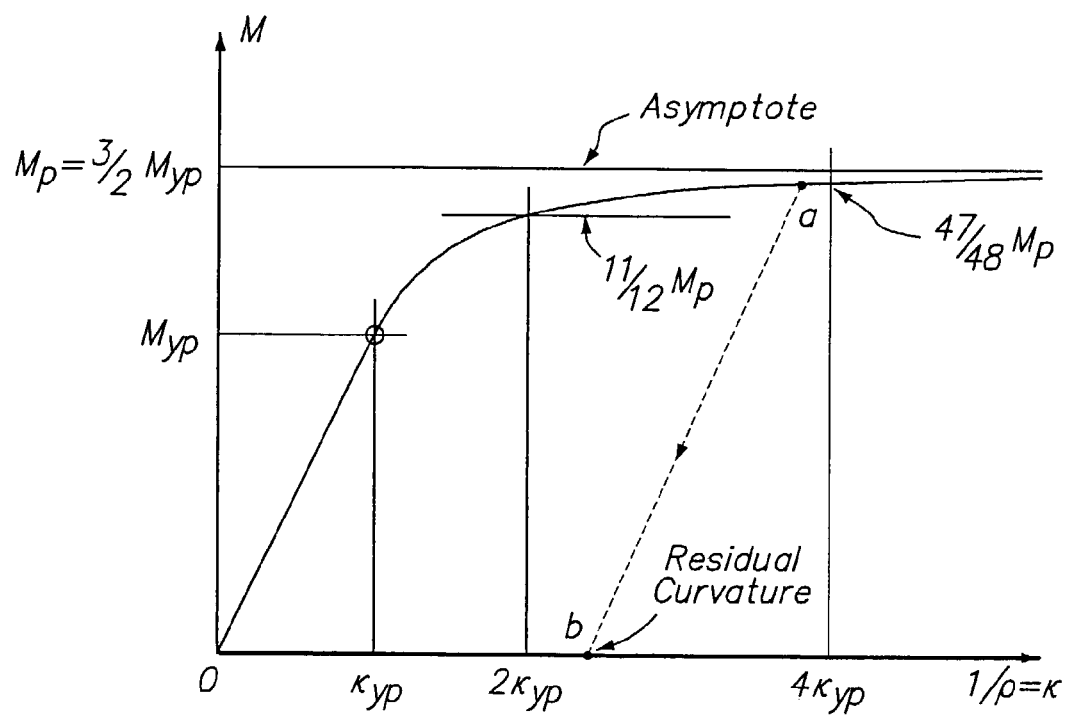
FIG. 7 is a moment verses curvature graph for a rectangular beam.

This function is plotted in FIG. 7. It may be seen in this plot that the applied moment M asymptotically approaches a limiting value $M_P$, called the plastic or ultimate moment. Beyond $^{11}/_{12} M_P$ large plastic deformations occur with little additional increase in applied moment. When the applied moment is removed, the beam rebounds elastically along a line such as a-b. Thus, the elastic portion of the total curvature approaches a limit of 3/2 the curvature at the yield point. These relations may be expressed as follows:

$$M_P = \frac{3}{2} M_{yp} \Rightarrow \kappa_{rebound} = \frac{3}{2} \kappa_{yp}$$

Imparting additional curvature in the plastic zone cannot further increase the elastic curvature, but will decrease the ratio of elastic to plastic curvature. Thus, additional curvature or larger expansion of the tissue supporting device will reduce the percentage recoil of the overall stent structure.

Figure 8:
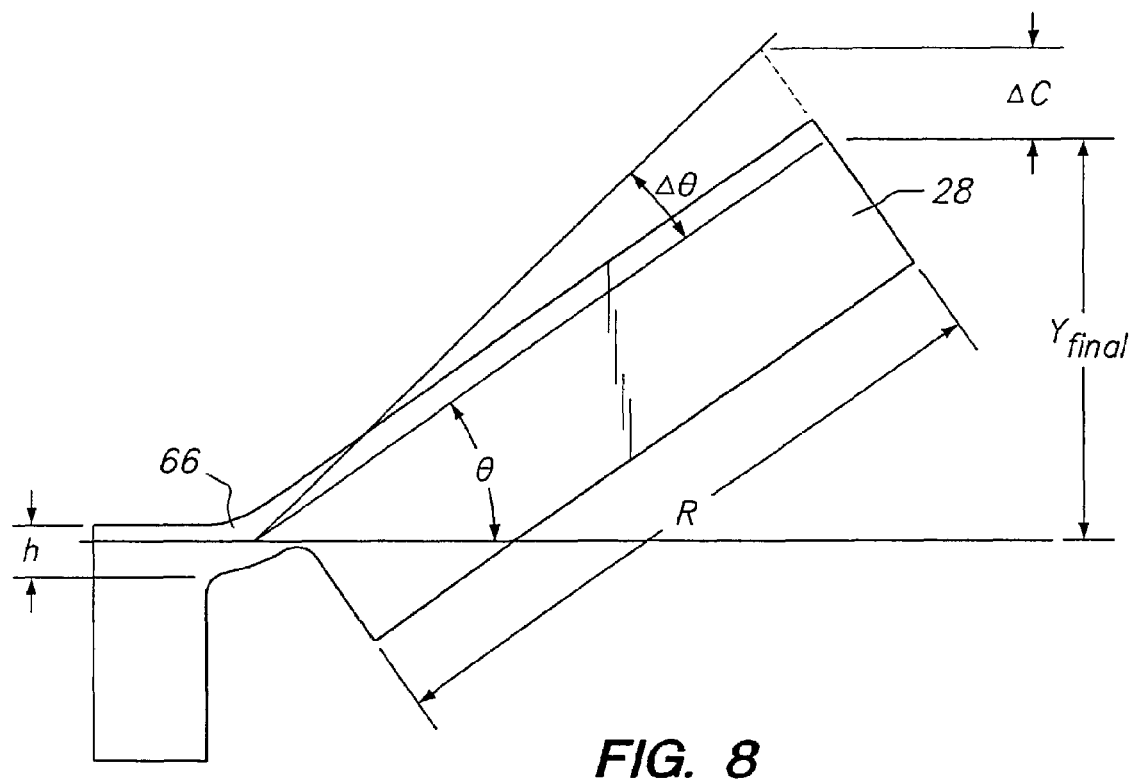
FIG. 8 is an enlarged side view of a bent ductile hinge.

As shown in FIG. 8, when a rigid strut 28 is linked to the ductile hinge 66 described above, the strut 28 forms an angle θ with the horizontal that is a function of hinge curvature. A change in hinge curvature results in a corresponding change in this angle θ. The angular elastic rebound of the hinge is the change in angle Δθ that results from the rebound in elastic curvature described above, and thus angular rebound also approaches a limiting value as plastic deformation proceeds. The following expression gives the limiting value of angular elastic rebound for the idealized hinge of FIG. 8.

$$\theta_{rebound} = 3 \epsilon_{yp} \frac{L}{h}$$

Where strain at the yield point is an independent material property (yield stress divided by elastic modulus); L is the length of the ductile hinge; and h is the width of the hinge. For non-idealized ductile hinges made of real materials, the constant 3 in the above expression is replaced by a slowly rising function of total strain, but the effect of geometry would remain the same. Specifically, the elastic rebound angle of a ductile hinge decreases as the hinge width h increases, and increases as the hinge length L increases. To minimize recoil, therefore, hinge width h should be increased and length L should be decreased.

Ductile hinge width h will generally be determined by expansion force criteria, so it is important to reduce hinge length to a practical minimum in order to minimize elastic rebound. Empirical data on recoil for ductile hinges of different lengths show significantly lower recoil for shorter hinge lengths, in good agreement with the above analysis.

The ductile hinges 32 of the tissue supporting device 20 provide a second important advantage in minimizing device recoil. The embodiment of FIG. 2 shows a network of struts-joined together through ductile hinges to form a cylinder. In this design, the struts 28 are initially parallel to an axis of the device. As the device is expanded, curvature is imparted to the hinges 32, and the struts 28 assume an angle θ with respect to their original orientation, as shown in FIG. 8. The total circumferential expansion of the tissue supporting device structure is a function of hinge curvature (strut angle) and strut length. Moreover, the incremental contribution to stent expansion (or recoil) for an individual strut depends on the instantaneous strut angle. Specifically, for an incremental change in strut angle Δθ, the incremental change in circumference ΔΘ will depend on the strut length R and the cosine of the strut angle θ.

ΔC=RΔθ cos θ

Since elastic rebound of hinge curvature is nearly constant at any gross curvature, the net contribution to circumferential recoil ΔC is lower at higher strut angles θ. The final device circumference is usually specified as some fixed value, so decreasing overall strut length can increase the final strut angle θ. Total stent recoil can thus be minimized with ductile hinges by using shorter struts and higher hinge curvatures when expanded.

Empirical measurements have shown that tissue supporting device designs based on ductile hinges, such as the embodiment of FIG. 2, display superior resistance to compressive forces once expanded despite their very low expansion force. This asymmetry between compressive and expansion forces may be due to a combination of factors including the geometry of the ductile hinge, the increased wall thickness, and increased work hardening due to higher strain levels.

According to one example of the tissue supporting device of the invention, the device can be expanded by application of an internal pressure of about 2 atmospheres or less, and once expanded to a diameter between 2 and 3 times the initial diameter can withstand a compressive force of about 16 to 20 gm/mm or greater. Examples of typical compression force values for prior art devices are 3.8 to 4.0 gm/mm.

While both recoil and crush strength properties of tissue supporting devices can be improved by use of ductile hinges with large curvatures in the expanded configuration, care must be taken not to exceed an acceptable maximum strain level for the material being used. For the ductile hinge 44 of FIG. 3b, for example, it may be shown that the maximum material strain for a given bend angle is given by the expression:

$$\epsilon_{max} = \frac{h}{L}\frac{\theta}{2}$$

Where $\epsilon_{max}$ is maximum strain, h is ductile hinge width, L is ductile hinge length and $\theta$ is bend angle in radians. When strain, hinge width and bend angle are determined through other criteria, this expression can be evaluated to determine the correct ductile hinge length L.

For example, suppose the ductile hinge 44 of FIG. 3b was to be fabricated of 316L stainless steel with a maximum strain of 30%; ductile hinge width h is set at 0.0025 inch (0.0635 mm) by expansion force criteria; and the bend angle $\theta$ is mechanically limited to 0.5 radians ($\cong$30%) at full stent expansion. Solving the above expression for L gives the required ductile hinge length of at least about 0.0033 inches (0.0838 mm).

Similar expressions may be developed to determine required lengths for more complicated ductile hinge geometries, such as shown in FIG. 3e. Typical values for the prismatic portions of these curved ductile hinges range from about 0.002 to about 0.0035 inches (0.051-0.089 mm) in hinge width and about 0.002 to about 0.006 inches (0.051-0.152 mm) in hinge length. The tissue supporting device design of FIGS. 4a and 4b include a stop which limits the maximum geometric deflection at the ductile hinges by the design of the angled walls 96 of the notches 94.

In many designs of the prior art, circumferential expansion was accompanied by a significant contraction of the axial length of the stent which may be up to 15% of the initial device length. Excessive axial contraction can cause a number of problems in device deployment and performance including difficulty in proper placement and tissue damage. Designs based on ductile hinges 32 can minimize the axial contraction, or foreshortening, of a tissue supporting device during expansion as follows.

Figure 9A:
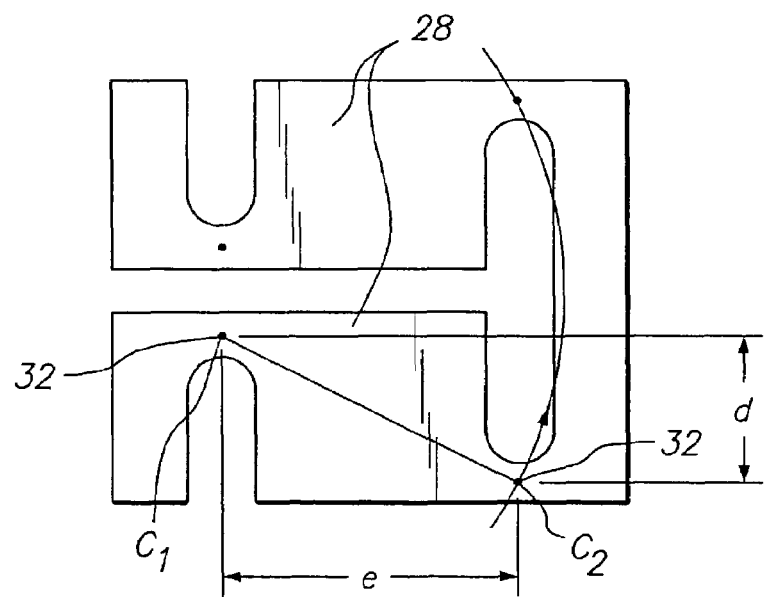
FIGS. 9a and 9b are enlarged side views of ductile hinges in initial and expanded positions with shortened struts to illustrate axial contraction relationships.
Figure 9B:
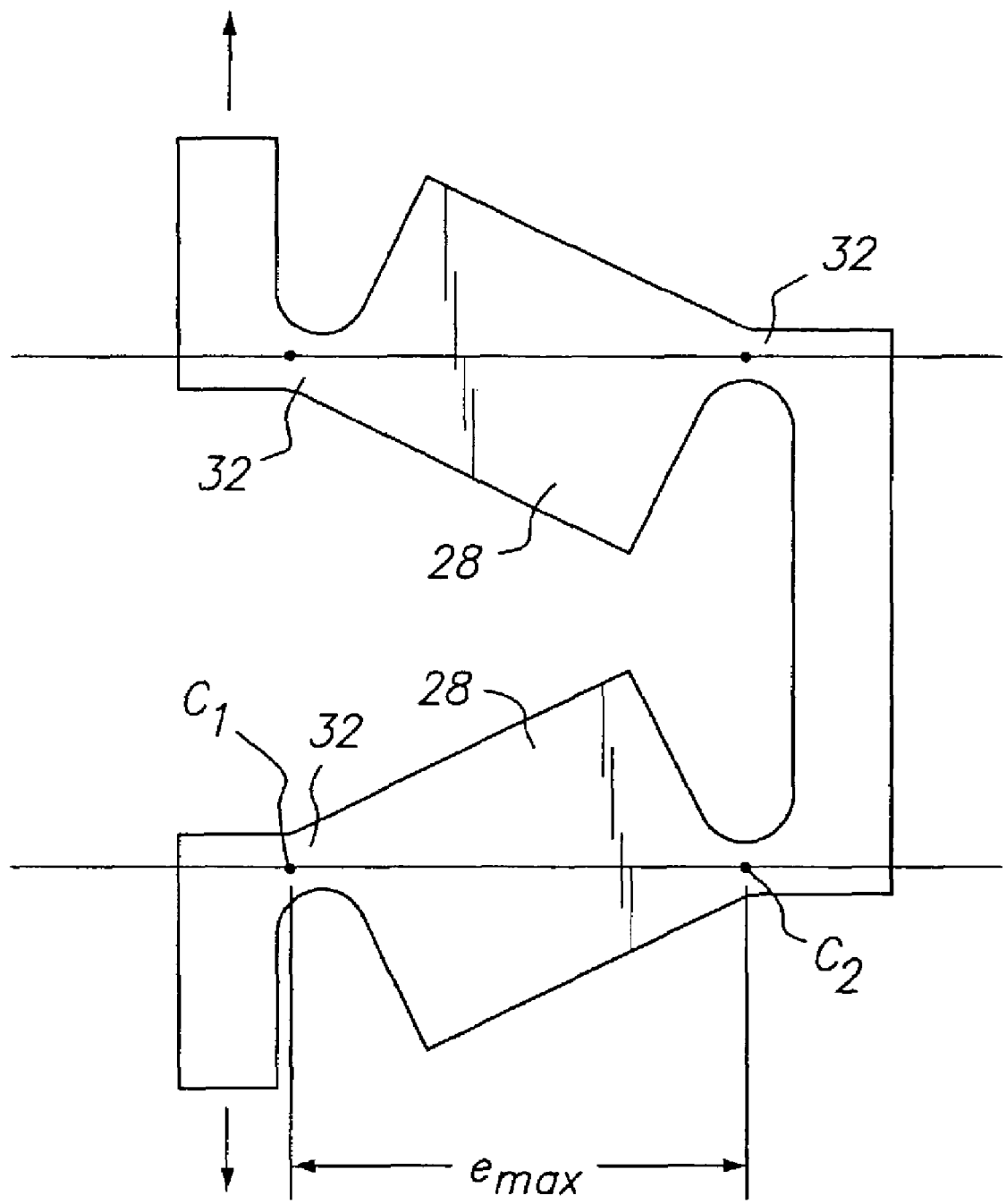

FIGS. 9a and 9b illustrate an exaggerated ductile hinge 32 and shortened struts 28 in initial and expanded conditions. Each strut 28 is attached to two ductile hinges 32 at opposite ends. Each ductile hinge 32 has an instant center of rotation $C_1$, $C_2$ that is an effective pivot point for the attached strut 28. Initially, during expansion the pivot point $C_1$ is displaced vertically by a distance d until $C_1$ is positioned even with $C_2$ as shown in FIG. 9b. When the array is expanded vertically, the axial struts 28 move in a circular arc with respect to the pivot points, as shown in FIG. 9b. It can be seen that the horizontal distance e between pivot points $C_1$ and $C_2$ actually increases initially, reaching a maximum $e_{max}$ when the two points are on the same horizontal axis as shown in FIG. 9b. As the vertical expansion continues, the device compresses axially back to its original length. Only when vertical expansion of the array continues beyond the point where the horizontal distance e between $C_1$ and $C_2$ is the same as the original horizontal distance e does the overall length of the array actually begin to contract. For the stent shown in FIG. 2, for example, approximately 1/3 of the total circumferential expansion has been accomplished by the time the configuration of FIG. 9b is reached, and the stent exhibits very low axial contraction.

This ability to control axial contraction based on hinge and strut design provides great design flexibility when using ductile hinges. For example, a stent could be designed with zero axial contraction.

Figure 10:
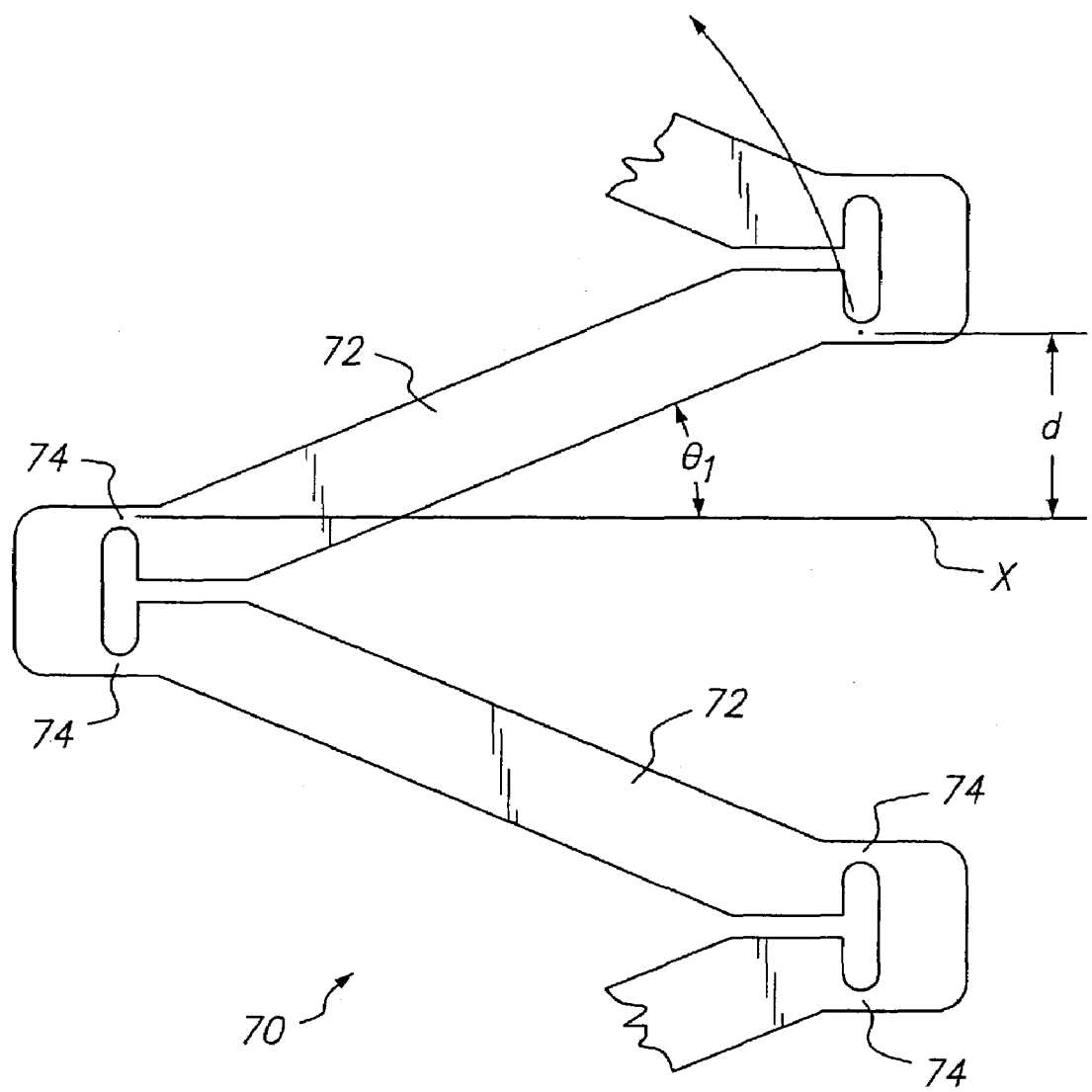
FIG. 10 is a side view of a portion of an alternative embodiment of a tissue supporting device having a high-crush-strength and low-recoil.

An alternative embodiment that illustrates the trade off between crush strength and axial contraction is shown in FIG. 10. FIG. 10 shows a portion of a tissue supporting device 70 having an array of struts 72 and ductile hinges 74 in the unexpanded state. The struts 72 are positioned initially at an angle $\theta_1$ with respect to a longitudinal axis X of the device. As the device is expanded radially from the unexpanded state illustrated in FIG. 10, the angle $\theta_1$ increases. In this case the device contracts axially from the onset of vertical expansion throughout the expansion. Once the device has been completely expanded the final angle $\theta_1$ made by the strut 72 with the horizontal will be much greater than the angle $\theta$ in the device of FIG. 8a and 8b. As shown previously, a higher final strut angle $\theta_1$, can significantly increase crush strength and decrease circumferential recoil of the stent structure. However, there is a trade off between increased crush strength and increase in axial contraction.

According to one example of the present invention, the struts 72 are positioned initially at an angle of about 0° to 45° with respect to a longitudinal axis of the device. As the device is expanded radially from the unexpanded state illustrated in FIG. 10, the strut angle increases to about 20° to 80°.

Figure 11:
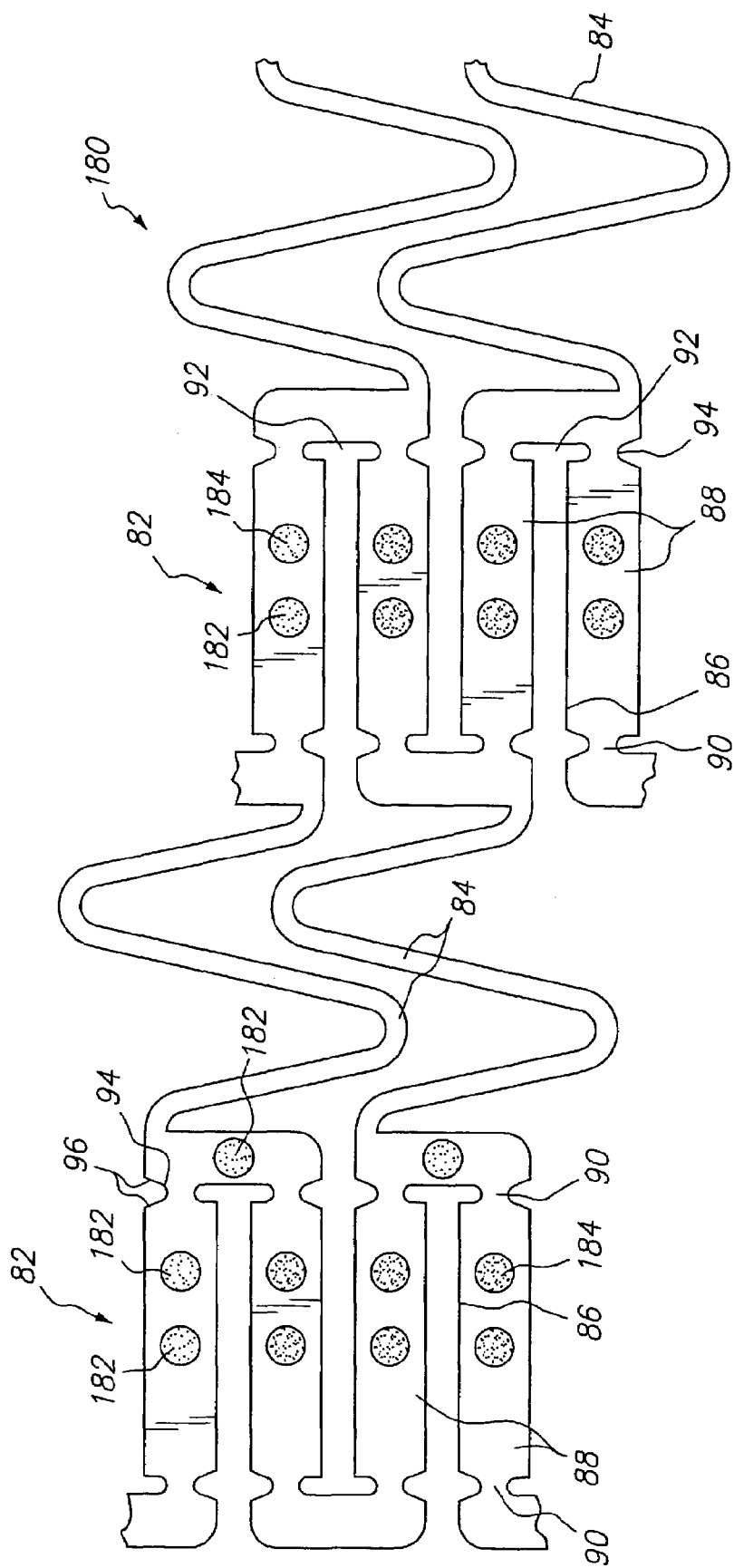
FIG. 11 is an enlarged side view of a tissue-supporting device in accordance with an alternative embodiment of the invention.

According to one alternative embodiment of the present invention, the expandable tissue supporting device can also be used as a delivery device for certain beneficial agents including drugs, chemotherapy, or other agents. Due to the structure of the tissue supporting device incorporating ductile hinges, the widths of the struts can be substantially larger than the struts of the prior art devices. The struts due to their large size can be used for beneficial agent delivery by providing beneficial agent on the struts or within the struts. Examples of beneficial agent delivery mechanisms include coatings on the struts, such as polymer coatings containing beneficial agents, laser drilled holes in the struts containing beneficial agent, and the like. Referring to FIG. 11, an alternative embodiment of a tissue supporting device is shown generally by reference number 180, with like reference numerals being used to denote like parts to those discussed above with respect to FIG. 4b. In addition, device 180 includes laser drilled holes 182 in the elongated beams or struts 88 for containing a beneficial agent 184.

While the invention has been described in detail with reference to the preferred embodiments thereof, it will be apparent to one skilled in the art that various changes and modifications can be made and equivalents employed, without departing from the present invention.

What is claimed is:

1. An expandable medical device comprising:
a plurality of elongated struts joined together to form a substantially cylindrical tube which is expandable from a cylinder having a first diameter to a cylinder having a second diameter;
a plurality of reduced area ductile hinges interconnecting the plurality of elongated struts, wherein the ductile hinges have a cross sectional area smaller than a cross sectional area of the elongated struts, and the ductile hinges deform upon expansion or compression of the cylindrical device while the struts are substantially undeformed; and
a plurality of holes containing a beneficial agent formed in the elongated struts;
wherein the ductile hinges have a substantially constant width in a circumferential dimension along a portion of a hinge length which is at least ⅓ the total length of a hinge.

2. The expandable medical device according to claim 1, wherein said beneficial agent is a drug.

3. The expandable medical device according to claim 1, wherein said beneficial agent includes chemotherapy drugs.

4. The expandable medical device according to claim 1, further comprising an abrupt transition between each of the elongated beams and each of the ductile hinges.

5. The expandable medical device according to claim 1, further comprising a plurality of axial slots between adjacent elongated beams and a plurality of circumferential slots, wherein the plurality of ductile hinges are each formed between an axial slot and a circumferential slot.

6. The expandable medical device according to claim 1, wherein the elongated beams have a thickness of at least 0.002 inch.

7. The expandable medical device according to claim 1, wherein the ductile hinges are asymmetrically configured to reach a predetermined strain level upon a first percentage expansion and to reach the predetermined strain level upon a second percentage of compression, the first percentage being larger than the second percentage.

8. The expandable medical device according to claim 1, wherein the struts have a thickness of at least 0.003 inch.

9. An expandable medical device comprising:
a plurality of elongated struts joined together to form a substantially cylindrical tube which is expandable from a cylinder having a first diameter to a cylinder having a second diameter;
a plurality of reduced area ductile hinges interconnecting the plurality of elongated struts, wherein the ductile hinges deform upon expansion or compression of the cylindrical device while the struts are substantially undeformed; and
a plurality of holes containing a beneficial agent formed in the elongated struts;
wherein the ductile hinges are asymmetrically configured to reach a predetermined strain level upon a first percentage expansion and to reach a predetermined strain level upon a second percentage of compression, the first percentage being larger than the second percentage.

10. The expandable medical device according to claim 9, wherein said beneficial agent is a drug.

11. The expandable medical device according to claim 9, wherein said beneficial agent includes chemotherapy drugs.

12. The expandable medical device according to claim 9, wherein the ductile hinges have a substantially constant width in a circumferential dimension along a portion of a hinge length which is at least ⅓ a total length, wherein the hinge width is smaller than the beam width such that as the device is expanded from the first diameter to the second diameter the ductile hinges do not experience plastic deformation while the beams are plastically deformed.

13. The expandable medical device according to claim 9, further comprising an abrupt transition between each of the elongated beams and each of the ductile hinges.

14. The expandable medical device according to claim 9, further comprising a plurality of axial slots between adjacent elongated beams and a plurality of circumferential slots, wherein the plurality of ductile hinges are each formed between an axial slot and a circumferential slot.

15. The expandable medical device according to claim 9, wherein the elongated beams have a thickness of at least 0.002 inch.

16. The expandable medical device according to claim 9, wherein the struts have a thickness of at least 0.003 inch.

* * * * *